US006733458B1

(12) United States Patent
Steins et al.

(10) Patent No.: US 6,733,458 B1
(45) Date of Patent: May 11, 2004

(54) DIAGNOSTIC MEDICAL ULTRASOUND SYSTEMS AND METHODS USING IMAGE BASED FREEHAND NEEDLE GUIDANCE

(75) Inventors: Robert W. Steins, Santa Clara, CA (US); Ann Shvarts, San Jose, CA (US); Thilaka S. Sumanaweera, Los Altos, CA (US)

(73) Assignee: Acuson Corporation, Mountain View, CA (US)

( * ) Notice: Subject to any disclaimer, the term of this patent is extended or adjusted under 35 U.S.C. 154(b) by 146 days.

(21) Appl. No.: 09/962,488

(22) Filed: Sep. 25, 2001

(51) Int. Cl.[7] .................................................. A61B 8/14
(52) U.S. Cl. ...................................................... 600/461
(58) Field of Search .............................. 600/407, 471, 600/564, 585; 606/40–205; 601/2, 3; 128/898, 916; 73/625, 626; 367/7, 11, 130, 138

(56) References Cited

U.S. PATENT DOCUMENTS

| 4,249,539 A | 2/1981 | Vilkomerson et al. ...... 128/660 |
| 4,407,294 A | 10/1983 | Vilkomerson ............... 128/660 |
| 5,161,536 A | 11/1992 | Vilkomerson et al. . 128/660.07 |
| 5,394,875 A | 3/1995 | Lewis et al. ........... 128/660.09 |
| 5,529,070 A | 6/1996 | Augustine et al. ..... 128/660.07 |
| 5,647,373 A | 7/1997 | Paltieli ........................ 128/749 |
| 5,660,185 A | 8/1997 | Shmulewitz et al. ....... 128/749 |
| 5,728,044 A | 3/1998 | Shan .......................... 600/145 |
| 5,793,701 A | 8/1998 | Wright et al. .................. 367/7 |
| 5,797,849 A | 8/1998 | Vesely et al. ............... 600/461 |
| 6,048,312 A | 4/2000 | Ishrak et al. ................ 600/443 |
| 6,122,538 A | 9/2000 | Sliwa, Jr. et al. ........... 600/407 |
| 6,216,029 B1 | 4/2001 | Paltieli ........................ 600/427 |

FOREIGN PATENT DOCUMENTS

WO   WO 99/27837   6/1999

OTHER PUBLICATIONS

PRNewswire news release via NewEdge Corporation re UltraGuide Patents Free–Hand Image Guidance System, Jul. 2, 2001, pp. 1–2.
UltraGuide Products US Guide "Free–hand Guidance for Ultrasound Interventions", obtained at http://www.ultraguide.co.il/products–us.html on Dec. 12, 2000, 4 pages.
Joyce Ward, article for Advance for Administrators in Radiology and Radiology Oncology, Jul. 1999, Cath–Lab Digest, "Sight Meets Sounds", obtained at http://www.ultraguide.co.il/news4.htm on Nov. 9, 1999, 8 pages.

*Primary Examiner*—Ali M. Imam

(57) ABSTRACT

A diagnostic medical ultrasound system having an integrated invasive medical device guidance system is disclosed. The guidance system obtains image slice geometry and other imaging parameters from the ultrasound system to optimize the guidance computations and visual representations of the invasive medical device and the imaged portion of the subject. Further, the ultrasound system obtains guidance data indicating the relative location, i.e. position and/or orientation of the invasive medical device relative to the transducer and imaging plane to optimize the imaging plane and ultrasound beam characteristics to automatically optimally image both the imaged portion of the subject and the invasive medical device.

27 Claims, 15 Drawing Sheets

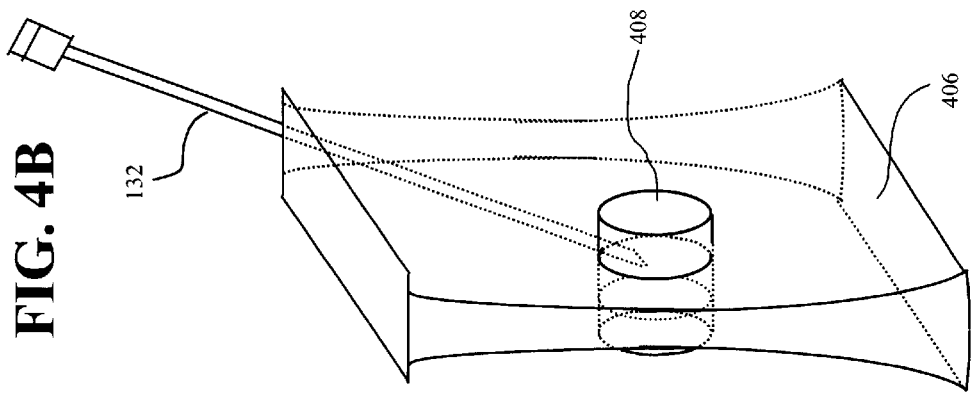
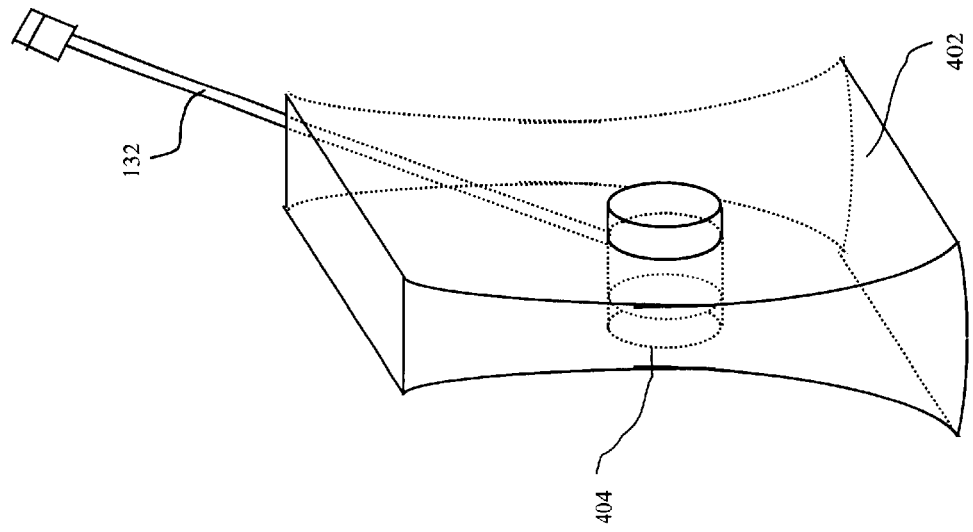

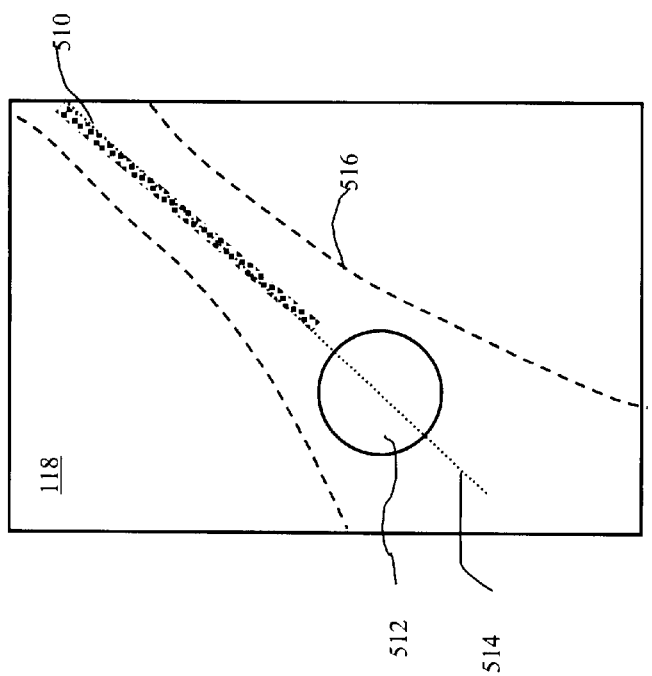
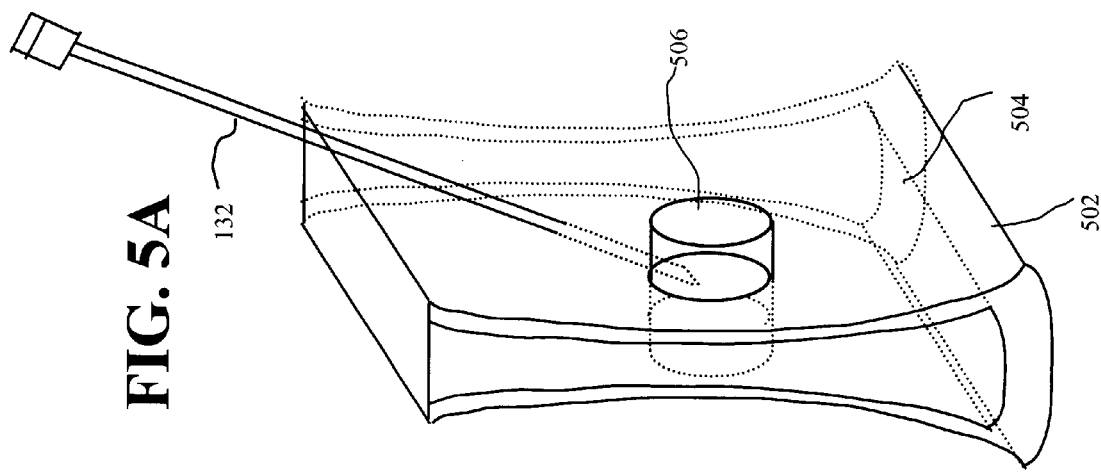

Ultrasound Image Display

Ultrasound Image Display

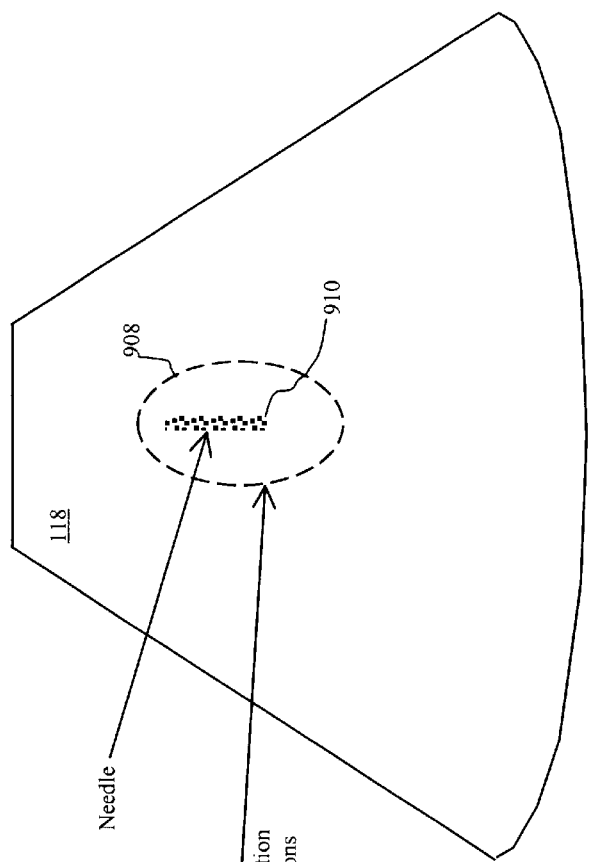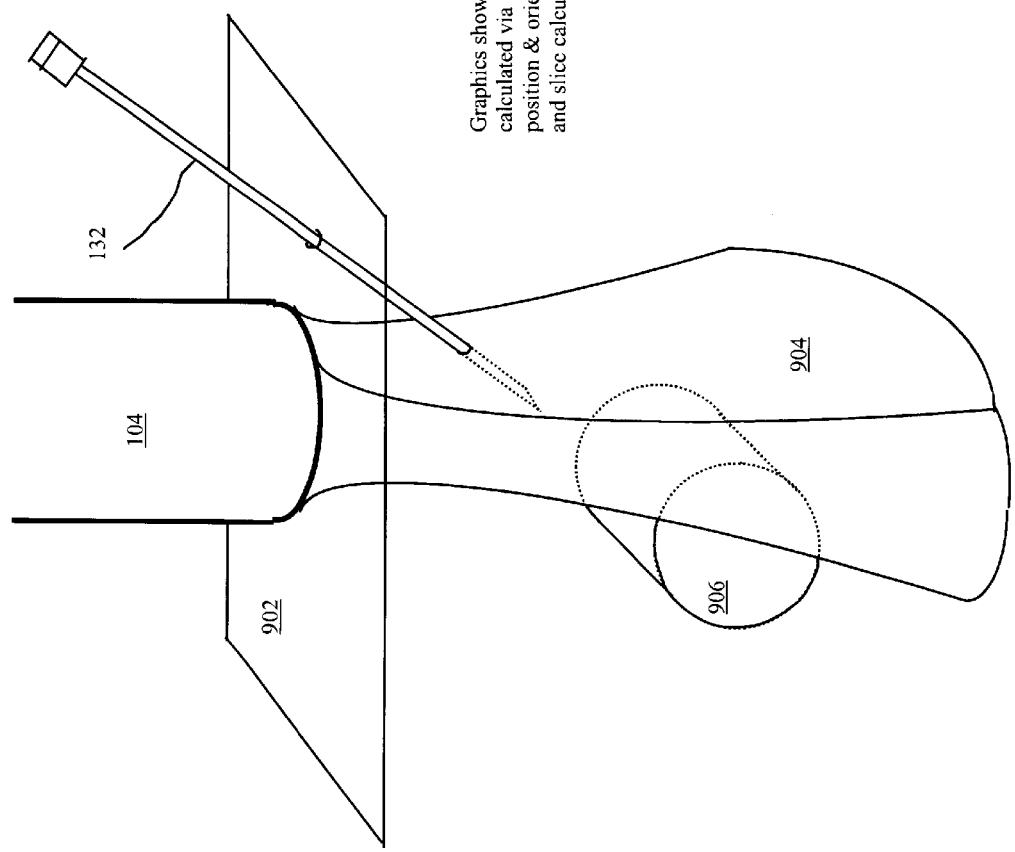

Two planes for visualization of the invasive device

Ultrasound Image Display of Figure 10

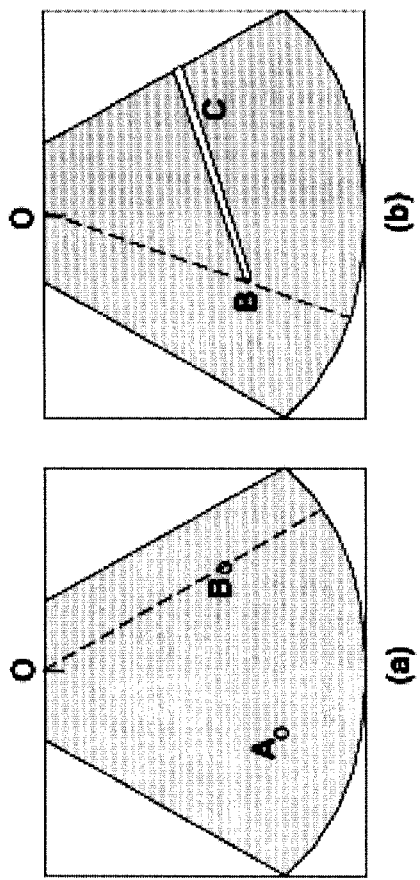
FIG. 15A
FIG. 15B
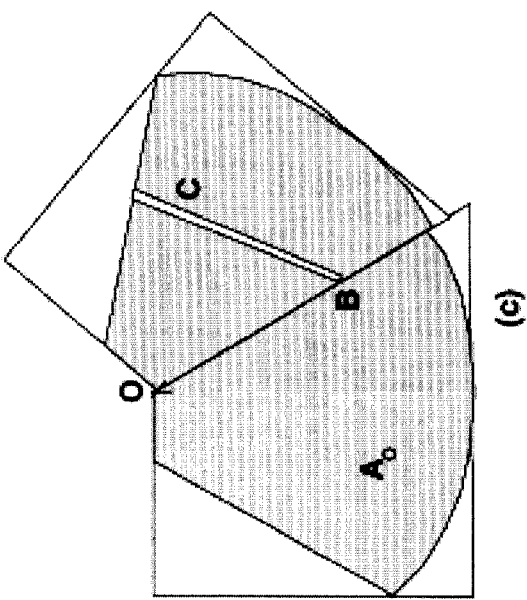
FIG. 15C

DIAGNOSTIC MEDICAL ULTRASOUND SYSTEMS AND METHODS USING IMAGE BASED FREEHAND NEEDLE GUIDANCE

BACKGROUND

Medical device guidance systems are used in medical applications for the purpose of guiding various types of invasive medical devices, such as aspiration and biopsy needles, endoscopes, etc., towards specific targets within a patient's body. These guidance systems simplify such procedures and make them safer and quicker to perform. In one example of guiding a biopsy needle using a free-hand method, a position sensor is affixed to the needle allowing the needle's absolute position in space to be determined. The region of the body in which the biopsy is to take place is imaged by an imaging system, such as ultrasound, CT or MRI. The absolute position of the imaging plane displayed by the imaging system is similarly determined using a position sensor affixed to the imaging apparatus and location techniques similar to that used for the needle. With the position information of the needle and of the imaging plane, the relative position of the needle with respect to the displayed imaging plane can be determined. From the relative position information, the projected or actual needle path is computed and is superimposed in real time on the displayed diagnostic image of the patient. This enables the physician to visualize the projected needle path and plan the biopsy procedure even before the needle is inserted into the body.

The following references relate to needle guidance systems: U.S. Pat. No. 5,647,373 to Paltieli, entitled "Articulated Needle Guide For Ultrasound Imaging and Method of Using Same"; PCT Application No. WO 99/27837 to Paltieli et al, entitled "System and Method For Guiding the Movements of a Device to a Target Particularly For Medical Applications"; and U.S. Pat. No. 6,216,029 to Paltieli, entitled "Free-Hand Aiming of a Needle Guide". An exemplary device which permits this type of free hand biopsy procedure is the Ultraguide 1000™ System manufactured by Ultraguide, Inc., located in Denver Colo. The Ultraguide 1000™ connects to an existing ultrasound system and provides a separate display device which superimposes graphical representations of the actual and projected needle trajectories over the ultrasound image.

While such devices provide a valuable diagnostic tool to physicians, they also suffer from inherent inaccuracies and may make invasive procedures of small or odd shaped targets at minimum difficult, if not impossible, to complete.

SUMMARY

The present invention is defined by the following claims, and nothing in this section should be taken as a limitation on those claims. By way of introduction, the preferred embodiments described below relate to a diagnostic medical ultrasound system. The system includes an invasive medical device and an ultrasound transducer operative to image a portion of a subject, the portion including a target for the invasive medical device. Further, the system includes a location calculator in communication with the ultrasound transducer and the invasive medical device and operative to determine the relative location of the invasive medical device and the ultrasound transducer. In addition, the system includes an image processor in communication with a display, the ultrasound transducer and the location calculator and operative to compute a first trajectory of the invasive medical device within the portion.

The preferred embodiments further relate to a method of displaying a projected and an actual trajectory of an invasive medical device relative to and within a portion of a subject for use in a diagnostic medical ultrasound system. In one embodiment, the method includes generating an image of the portion utilizing an ultrasound transducer, obtaining location information about the ultrasound transducer and the invasive medical device, computing a first trajectory of the invasive medical device relative to the portion utilizing the location information, and computing a second trajectory of the invasive medical device within the portion utilizing the location information.

Further aspects and advantages of the invention are discussed below in conjunction with the preferred embodiments.

BRIEF DESCRIPTION OF THE DRAWINGS

FIG. 4A depicts a representation of an invasive procedure and ultrasonic beam profile in the presence of a biopsy device and target.

FIG. 4B depicts a representation of an invasive procedure and ultrasonic beam profile as modified by a third embodiment.

FIG. 5A depicts a representation of an invasive procedure and interleaved ultrasonic beam profile according to the third embodiment.

FIG. 5B depicts a representation of a diagnostic medical ultrasound image of the invasive procedure of FIG. 5A.

FIG. 9A depicts a second representation of the invasive procedure of FIG. 8A showing an ultrasonic beam profile orthogonal to the beam profile depicted in FIG. 8A, according to the fifth embodiment.

FIG. 9B depicts a graphical representation of a diagnostic medical ultrasound image corresponding to the beam profile shown in FIG. 9A, according to the fifth embodiment.

FIGS. 15A–C depicts a graphical representation of diagnostic medical ultrasound image plane displays according to the seventh embodiment.

DETAILED DESCRIPTION OF THE PRESENTLY PREFERRED EMBODIMENTS

Figure 1:
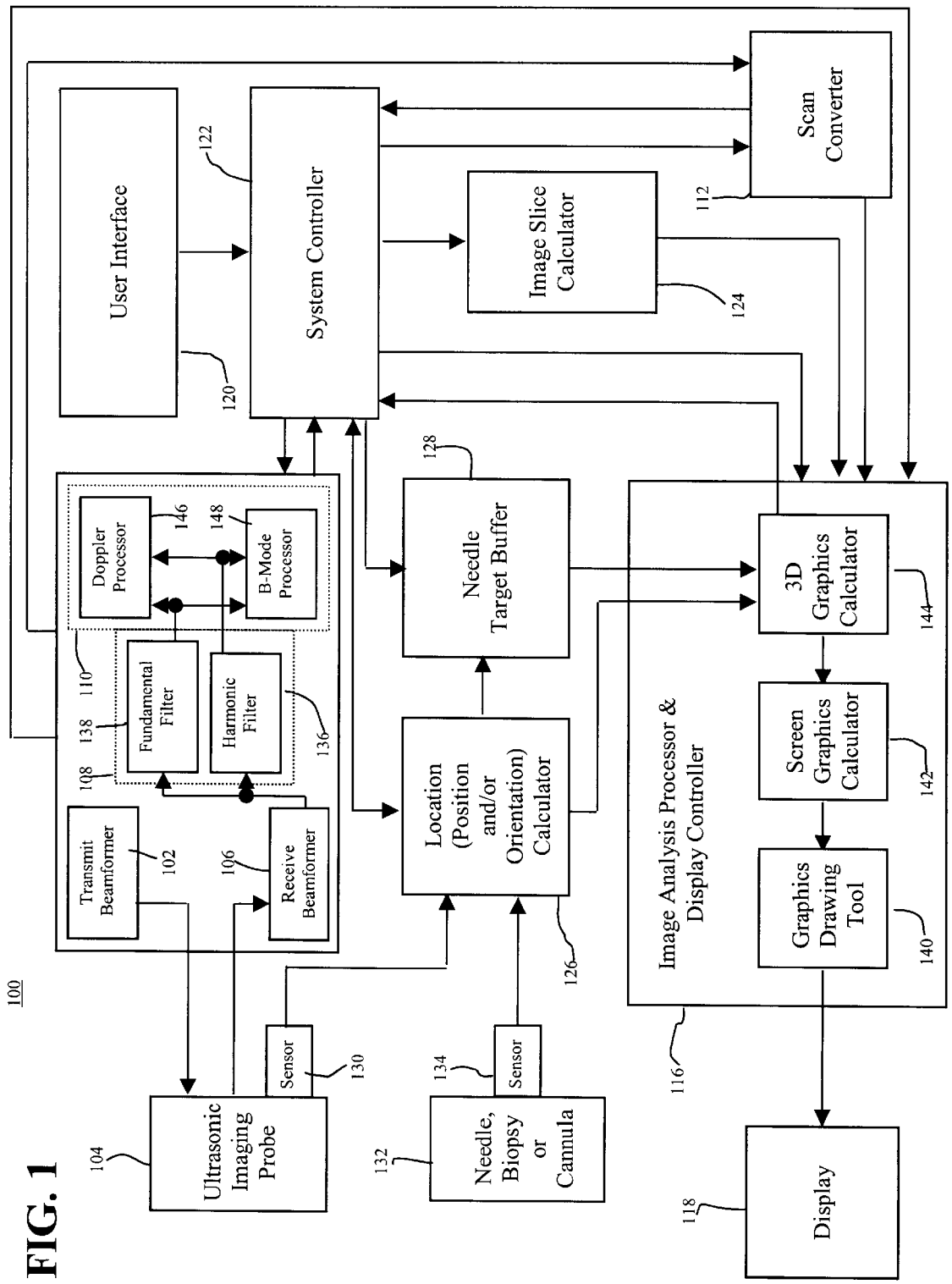
FIG. 1 depicts a block diagram of one embodiment of a diagnostic medical ultrasound system according to the present invention.

In one known embodiment of an invasive medical device guidance system, the system is separate from the medical imaging system, such as a diagnostic medical ultrasound system, which is used to display the target. The guidance system connects to the imaging system, such as via a video output port, and utilizes the images generated by the imaging system to create further representations showing actual and projected device guidance information. To create these representations of the trajectory of the invasive medical device, such as a needle, to a target inside the patient's body, the guidance system superimposes a graphical representation of the actual and/or projected trajectory of the device over the externally supplied ultrasound images. The trajectories, actual or projected, are computed from known position information determined by sensors on the medical device and on the ultrasound transducer. Alternatively, other methods known in the art can be used to determine the position information. This allows the guidance system to merge the two dimensional ultrasound images obtained from the ultrasound system with a graphically represented image of the needle trajectory and display this merged image to the physician or sonographer.

One problem with such systems, especially where diagnostic ultrasound is utilized as the medical imaging system, is that the area of the body imaged by the ultrasound transducer is not, strictly speaking, a flat plane as shown on the display and provided to the external guidance system as described above. An ultrasound transducer images a slice through the body having a width, depth and thickness (typically described using the azimuth, range and elevation dimensions, respectively). These dimensions are a function of the transducer construction and ultrasound beam formation and are largely dependent on the desired focal point to be achieved for imaging a particular portion of a subject. The construction of an ultrasound transducer and beam former, in the case of a transducer with a fixed elevation, or elevation configuration settings, in the case of a transducer with an active elevation, must consider the best slice thickness for a particular clinical application such as imaging the abdomen vs. a thyroid gland. In the case of the abdominal transducer, the elevation plane will normally be thicker and usually focused deeper because the targeted abdominal contents are larger and more difficult to penetrate. A thicker and more deeply focused slice improves the ability of the transducer to transmit larger amounts of ultrasound energy into the body therefore improving the amount of returned energy for processing. This is in contrast to the thyroid gland which is considerably more superficial and smaller in size thereby allowing a thinner and shallower elevation focus to be utilized. In general it is always desired to have as thin a slice profile as possible, yet maintaining an acceptable level of penetration of the desired anatomy. As the penetration needs are increased, the ultrasound slice tends to thicken therefore increasing the amount of volume insonated. Using known algorithms, such as volume averaging, the image processor of the ultrasound system essentially flattens the returned ultrasound data in the elevation dimension when the image is ultimately rendered as a two-dimensional representation on a video display or other output device. This may lead to some distortion of the structures being imaged or create slice artifacts which decrease the clarity of the image. As the elevation thickness grows to meet a clinical application's needs, the ambiguity in the displayed image when attempting to determine the location of a structure is increased.

A guidance system which fails to take into account this slice geometry will similarly misrepresent, i.e. render inaccurate/ambiguous representations of, the actual or projected intersections of the invasive medical devices with the other structures imaged in the imaging plane. This is especially apparent for very small targets, oddly shaped targets, or targets surrounded by critical tissue or organs. In these cases, the elevation resolution of the ultrasound transducer, a function of the slice thickness, is a factor in accurately guiding the invasive medical device. The inability to optimize the needle guidance to account for slice geometry and other ultrasound parameters reduces the clinician's ability to successfully complete an ultrasound image guided procedure due to a more limited ability to visualize the invasive device.

Another problem with non-integrated imaging and guidance systems is that, often, the image plane or scan area of the imaging system, such as an ultrasound system, is generated at a sub-optimal imaging angle to said invasive medical device, generated out of plane with the invasive device, or otherwise generated in a less than optimal fashion, which prevents optimal imaging of both the target and the invasive device simultaneously. It will be appreciated that invasive devices are more visible when they lie within the imaging plane/scan area, i.e. along the azimuth direction, and perpendicular to the emitted acoustic signals, i.e. perpendicular to the range direction, of an ultrasound transducer. In some cases, it may be impossible, due to the location of the target, to image both the target and the invasive device in a single imaging plane/scan area. This requires the clinician to reposition either the ultrasound transducer, the invasive device or both in order to best visualize the target and/or the invasive device. While the guidance system typically provides feedback via the user interface to allow the clinician to optimize this positioning, the need to reposition the equipment is still a tedious and time consuming task. In addition, where both the target and the invasive device cannot be imaged in the same plane/scan area, the clinician may be forced to constantly reposition the transducer and/or invasive device to achieve an acceptable view of the procedure. Further, the clinician may settle for sub-optimal positioning, and therefore viewing, so as not to waste too much time or make the subject too uncomfortable to complete the actual procedure in a timely fashion.

FIG. 1, shows one embodiment of an ultrasound system 100 including an integrated invasive medical device guidance system. It will be appreciated that one or more of the described components may be combined as a single component and that one or more of the components may be implemented completely in hardware, software or a combination thereof. Computation and rendering of the actual and projected device trajectories is performed using image and image slice geometry data acquired as a function of the transducer. The actual trajectory is the trajectory that the device is currently taking, accounting for its current location (position and orientation). The projected trajectory is computed as the trajectory the device will take if it maintains its current orientation while being advanced or retarded in position. This permits image data and slice geometry to be acquired and factored into the guidance calculations. Such low level image and slice data includes the geometric attributes of the image slice such as the slice thickness, the frequency, the dimensions of the scanned plane, the scanning format and calibration data. Further, guidance calculations indicating the position and/or orientation of the invasive device and transducer are fed back to the system controller to automatically optimize the image plane for optimal viewing.

The ultrasound system 100 of FIG. 1 includes a transmit beamformer 102, an ultrasonic imaging probe or transducer 104, a receive beamformer 106, a filter block 108, a signal processor 110, a scan converter 112, an image data storage 114, an image processor 116 and a display 118. Alternatively, as described below, other types of transmitters and/or receivers may be used. The exemplary ultrasound system 100 is configurable to acquire information corresponding to a plurality of two-dimensional representations or image planes of a subject for three-dimensional reconstruction. Other systems, such as those for acquiring data with a two dimensional, 1.5 dimensional or single element transducer array, may be used. To generate each of the plurality of two-dimensional representations of the subject during an imaging session, the ultrasound system 100 is configured to transmit, receive and process during a plurality of transmit events. Each transmit event corresponds to firing acoustic energy along one or more ultrasound scan lines in the subject.

The transmit beamformer 102 is of a construction known in the art, such as a digital or analog based beamformer capable of generating signals at different frequencies. The transmit beamformer 102 generates one or more excitation signals. Each excitation signal has an associated center frequency. As used herein, the center frequency represents the frequency in a band of frequencies approximately corresponding to the center of the amplitude distribution. Preferably, the center frequency of the excitation signals is within the 1 to 15 MHz range and accounts for the frequency response of the transducer 104. The excitation signals have non-zero bandwidth.

It will be appreciated that alternative methods of generating and controlling ultrasonic energy as well as receiving and interpreting echoes received therefrom for the purpose of diagnostic imaging, now or later developed, may also be used with the disclosed embodiments in addition to or in substitution of current beam-forming technologies. Such technologies include technologies which use transmitters and/or receivers which eliminate the need to transmit ultrasonic energy into the subject along focused beam lines, thereby eliminating the need for a transmit beamformer, and may permit beam forming to be performed by post processing the received echoes. Such post-processing may be performed by a receive beamformer or by digital or analog signal processing techniques performed on the received echo data. For example, please refer to U.S. patent application Ser. No. 09/518,972, entitled "METHODS AND APPARATUS FOR FORMING MEDICAL ULTRASOUND IMAGES," now U.S. Pat. No. 6,309,356, and U.S. patent application Ser. No. 09/839,890, entitled "METHODS AND APPARATUS FOR FORMING MEDICAL ULTRASOUND IMAGES," now U.S. Pat. No. 6,551,246, the disclosures of which are herein incorporated by reference.

Upon the firing of one or more ultrasound scan lines into the subject, some of the acoustical energy is reflected back to the transducer 104. In addition to receiving signals at the fundamental frequency (i.e., the same frequency as that transmitted), the non-linear characteristics of tissue or optional contrast agents also produce responses at harmonic frequencies. Harmonic frequencies are frequencies associated with non-linear propagation or scattering of transmit signals. As used herein, harmonic includes subharmonics and fractional harmonics as well as second, third, fourth, and other higher harmonics. Fundamental frequencies are frequencies corresponding to linear propagation and scattering of the transmit signals of the first harmonic. Non-linear propagation or scattering corresponds to shifting energy associated with a frequency or frequencies to another frequency or frequencies. The harmonic frequency band may overlap the fundamental frequency band.

The filter block 108 passes information associated with a desired frequency band, such as the fundamental band using fundamental band filter 138 or a harmonic frequency band using the harmonic band filter 136. The filter block 108 may be included as part of the receive beamformer 106. Furthermore, the fundamental band filter 138 and the harmonic band filter 136 preferably comprise one filter that is programmable to pass different frequency bands, such as the fundamental, second or third harmonic bands. For example, the filter block 108 demodulates the summed signals to baseband. The demodulation frequency is selected in response to the fundamental center frequency or another frequency, such as a second harmonic center frequency. For example, the transmitted ultrasonic waveforms are transmitted at a 2 MHz center frequency. The summed signals are then demodulated by shifting by either the fundamental 2 MHz or the second harmonic 4 MHz center frequencies to baseband (the demodulation frequency). Other center frequencies may be used. Signals associated with frequencies other than near baseband are removed by low pass filtering. As an alternative or in addition to demodulation, the filter block 108 provides band pass filtering. The signals are demodulated to an intermediate frequency (IF)( e.g. 2 MHz) or not demodulated and a band pass filter is used. Thus, signals associated with frequencies other than a range of frequencies centered around the desired frequency or an intermediate frequency (IF) are filtered from the summed signals. The demodulated or filtered signal is passed to the signal processor 110 as the complex I and Q signal, but other types of signals, such as real value signals, may be passed.

By selectively filtering which frequencies are received and processed, the ultrasound system 100 produces images with varying characteristics. In tissue harmonic imaging, no additional contrast agent is added to the target, and only the nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no contrast agent is introduced into the tissue at any time during the imaging session.

Tissue harmonic images provide a particularly high spatial resolution and often possess improved contrast resolution characteristics. In particular, there is often less clutter in the near field. Additionally, because the transmit beam is generated using the fundamental frequency, the transmit beam profile is less distorted by a specific level of tissue-related phase aberration than a profile of a transmit beam formed using signals transmitted directly at the second harmonic.

The harmonic imaging technique described above can be used for both tissue and contrast agent harmonic imaging. In contrast agent harmonic imaging, any one of a number of well known nonlinear ultrasound contrast agents, such as micro-spheres or the Optison™ agent by Nycomed-Amersham of Norway, are added to the target or subject in order to enhance the non-linear response of the tissue or fluid. The contrast agents radiate ultrasonic energy at harmonics of an insonifying energy at fundamental frequencies.

The signal processor 110 comprises one or more processors for generating two-dimensional Doppler or B-mode information. For example, a B-mode image, a color Doppler velocity image (CDV), a color Doppler energy image (CDE), a Doppler Tissue image (DTI), a Color Doppler Variance image, or combinations thereof may be selected by a user. The signal processor 110 detects the appropriate information for the selected image. Preferably, the signal processor 110 comprises a Doppler processor 146 and a B-mode processor 148. Each of these processors is preferably a digital signal processor and operates as known in the art to detect information. As known in the art, the Doppler processor 146 estimates velocity, variance of velocity and energy from the I and Q signals. As known in the art, the B-mode processor 148 generates information representing the intensity of the echo signal associated with the I and Q signals.

The information generated by the signal processor 110 is provided to the scan converter 112. Alternatively, the scan converter 112 includes detection steps as known in the art and described in U.S. Pat. No. 5,793,701 entitled "METHOD AND APPARATUS FOR COHERENT IMAGE FORMATION", assigned to the assignee of the present invention, the disclosure of which is herein incorporated by reference. The scan converter 112 is of a construction known in the art for arranging the output of the signal processor 110 into two-dimensional representations or frames of image data. The scan converter 112 converts acoustic ultrasound line data, typically in a polar coordinate system, into data which may be plotted on a Cartesian grid. Using volume averaging or other similar algorithms on the returned echo data, the slice information is merged into a single 2D plane. This permits display of the ultrasound image on a two-dimensional output device such as a display monitor. Preferably, the scan converter 112 outputs formatted video image data frames, using a format such as the DICOM Medical industry image standard format or a TIFF format. Thus, the plurality of two-dimensional representations are generated. Each of the representations corresponds to a receive center frequency, such as a second harmonic center frequency, a type of imaging, such as B-mode, and positional information. The harmonic based representations may have better resolution and less clutter than fundamental images. By suppressing the harmonic content of the excitation signal, the benefits of harmonic imaging of tissue may be increased.

The system 100 further includes a first sensor 130 coupled with the ultrasound imaging probe 104, a user interface 120, a system controller 122, a second sensor 134 coupled with an invasive medical device 132, a location (position and/or orientation) calculator 126, a needle target buffer 128, and an image slice calculator 124. Herein, the phrase "coupled with" is defined to mean directly connected to or indirectly connected through one or more intermediate components. Such intermediate components may include both hardware and software based components. Further, as used herein, the term "location" is used to refer to an object's spatial position, orientation or both. Generally, an object's position is a representation of the area or volume that it occupies in absolute or relative relation to a known origin or reference or within a known coordinate system, e.g. linear distance from the patient. An object's orientation is a representation of its arrangement/alignment in space within its position in absolute or relative relation to a known origin or reference, e.g. angle relative to the floor. It will be appreciated that there may be many ways to define an objects location (position and/or orientation) within a given space. The image processor 116 further includes a graphics drawing tool 140, a screen graphics calculator 142 and a 3D graphics calculator 144.

The user interface 120 includes an input device which the clinician/sonographer/physician uses to interface with the ultrasound system 100, including the needle guidance system. The user interface 120 includes input devices such as a keyboard, mouse, trackball, touch screen or other input devices or combinations thereof as are known in the art. Further the user interface 120 may also include graphic user interface ("GUI") elements coupled with the input devices and with the display 118 for both input and output functions. In addition to controlling the ultrasound functions of the ultrasound system 100, the user interface 120 supplies the user with control functions for operation and calibration of the needle guidance functionality. For example, the clinician may use the ultrasound system for many examinations that do not require an invasive device 132, therefore, the user interface 120 would allow the clinician to activate or deactivate the needle guidance and visualization system as needed. Additionally, controls are provided by the user interface 120 for calibration of the subsystems included in the needle guidance and visualization system. Also, the user interface 120 may afford the user the opportunity to modify graphical representations, imaging planes and displays produced by the ultrasound system 100 to enhance the operation of the needle guidance and visualization subsystems. Finally, the user interface 120 allows the user to coordinate multiple ultrasound probes 104 each coupled with its own sensor 130, and/or multiple invasive devices 132, each coupled with its own sensor 134 for complex guidance procedures.

The system controller 122 controls and coordinates the functions of the ultrasound and guidance subsystems. In one embodiment, the system controller includes The term "system controller" broadly refers to the appropriate hardware and/or software components of the ultrasound system 100 that can be used to implement the preferred embodiments described herein. It should be understood that any appropriate hardware (analog or digital) or software can be used and that the embodiments described herein can be implemented exclusively with hardware. Further, the system controller 122 can be separate from or combined with (in whole or in part) other processors of the ultrasound system 100 (including attendant processors), which are not shown in FIG. 1 for simplicity.

The various elements of the ultrasound system including the transmit beamformer 102, the receive beamformer 106, harmonic filter 136, fundamental filter 138, image analysis processor & display controller 116, Doppler processor 146, B-mode processor 148, user interface 120, and scan converter 112 are controlled in real time by the system controller 122. The controller 122 controls the operation of the components of the system 100. A user, via the user interface 120, can adjust imaging parameters such as, but not limited to, image depth, image width, and frame rate. The controller 122 interprets the set-up information entered by the user and configures the components of the system 100 accordingly. An exemplary commercially available ultrasonic imaging system for use with the disclosed embodiments is the Sequoia 512 system manufactured by Acuson Corporation of Mountain View, Calif.

In the disclosed embodiments, the image slice calculator 124, needle target buffer 128, location (position and/or orientation) calculator 126 are also coupled with the controller 122 such that the relative or absolute position and/or orientation of the transducer 104 and invasive device(s) 132 is now accessible to the ultrasound system 100 as described herein.

Location sensors 130, 134 are sensors capable of sensing location, i.e. position, orientation or both parameters and generating data representing the location, i.e. position, orientation, or both, of the sensor 130, 134 and whatever the sensor 130, 134 is attached to, i.e. the probe 104 or invasive device 132. More than one sensor 130, 134 may be provided wherein one sensor 130, 134 senses position while the other senses orientation. The sensor 130 may be internal or external to the probe 104.

In one embodiment, the probe 104 includes an ultrasonic imaging transducer array with the capability, either mechanically or electronically, of beam steering in the azimuth, elevation or both dimensions, elevation beam focusing or combinations thereof. The array may have an active or fixed elevation geometry. An active elevation geometry permits both beam steering and elevation focusing. Elevation beam focusing differs from beam steering typically by the amount of active independent channels (and piezoelectric elements) devoted to beam formation; focusing is a subset of beam steering. When one speaks of a "2D array", the transducer is beam steerable in elevation while a transducer with active elevation may not be beam steerable but is capable of focusing in elevation.

The invasive medical device or implement 132 may be a needle, cannula, catheter, probe or other type of invasive device including biopsy devices. The device 132 is fitted with one or more location sensors 134. The device may be further fitted with sensors which detect deformation, such as strain gauges or other force sensors. An exemplary device which detects such deformation is a colonoscope as described in U.S. Pat. No. 5,728,044 to Shan, the disclosure of which is herein incorporated by reference.

The location sensors 130, 134 may be attached to the transducer 104 or invasive device 132 or may be integral. Further, the sensors 130, 134 may operate by optical, magnetic, gyroscopic, accelerometric or other means or any combination thereof. In addition, the sensors 130, 134 may be wired or wireless, active or passive. Exemplary medical device location systems are described in more detail in U.S. Pat. No. 5,529,070 to Augustine et al and in commonly assigned U.S. Pat. No. 6,122,538, entitled "MOTION MONITORING METHOD AND SYSTEM FOR MEDICAL DEVICES" to Sliwa et al, the disclosures of which are herein incorporated by reference.

The location calculator 126 determines the absolute and/or relative position and/or orientation of the transducer 104 and the invasive medical device 132. In one embodiment, the location calculator 126 computes position only, such as when using a flexible catheter where only the position of the catheter tip need be known. In another embodiment, the location calculator 126 determines both position and orientation, such as for a rigid invasive device 132 where the angle of the device 132 must be determined. Alternatively, the location calculator 126 can determine the position and/or orientation of multiple transducers 104, multiple invasive medical devices 132 or combinations thereof. The output of the location calculator 126 is sent to the needle target buffer 128 and the 3D graphics calculator 144.

The 3D graphics calculator 144 computes the projected and actual trajectories of the invasive medical device(s) 132 and the intersection of the device(s) 132 with the portion of the subject represented by the ultrasonic image. Three-dimensional (X, Y, Z) axis data is maintained for this calculation. The 3D graphics calculator 144 receives inputs from the location calculator 126, the needle target buffer 128 and the image slice calculator 124. The output of the 3D graphics calculator 144 goes to the screen graphics calculator 142 which coverts the trajectory data to graphical representations that can be super imposed on the image/display 118. The output of the 3D graphics calculator 144 also goes to the system controller 122 and may be used to align the imaging transducer's 104 scan area, elevation profile and/or beam orientation for optimal visualization of the invasive medical device(s) 132. Alternatively, the output of the location calculator 126 may be used by the system controller 122 for re-orienting the image plane as will be described below. This alignment may be under the clinician's control or may be automatically performed to optimize the visualization of the device 132 and the target for the given procedure.

The image slice calculator 124 receives information from the system controller 122 about the imaging attributes of the transducer or those attributes being used or changed by the sonographer via the user interface 120. This attribute information is used by the image slice calculator 124 to take into account changing image slice characteristics due to, but not limited to, frequency, transmit focus location, scan area and the subsequent effect of these variables on the image slice geometry. In one embodiment of the invention, the slice thickness may be acquired from calibration or reference data stored in the slice thickness calculator. This calibration/reference data may be determined from pre-acquired measurement data that has been loaded as part of the imaging control/configuration data when a transducer is activated. The measurement data may be generated in several ways including theoretical or water tank analysis of the elevational pressure profile. The image slice calculator 124 determines the slice thickness of the current image by utilizing the controller information, including beam formation parameters, the user interface 120 settings, and the slice reference data. The image slice calculation data is sent to the image processor 116 for integration of the position and/or orientation information for the 3D graphics calculation of the device 132 trajectory and the slice orientation.

The needle target buffer 128 receives input from the location calculator 126 and the user interface 120 via the system controller 122. The needle target buffer 128 enables the system 100 to graphically display the area of the subject, via the ultrasound image, into which the invasive device(s) 132 will be placed. The needle target buffer 128 computes the location of transducer 104, the imaging plane produced therefrom and the invasive device 132 and generates image data which can be merged with the displayed ultrasound image. The needle target buffer 128 factors in position and/or orientation accuracy and device 132 deformation. The needle target buffer 128 stores reference data regarding the tolerances and/or error in the position and/or orientation data returned by the location sensors 130, 134 and also the potential deflection of the invasive device 132 being used. Since there may be error in the accuracy of the location sensors 130, 134 or potential deflection of the invasive device 132, it is important to convey this error in the graphical display of the needle trajectory to the clinician performing the biopsy. This error potential is computed by the needle target buffer 128 and, in one embodiment, may be graphically represented to the clinician by demarcated regions of confidence of where the invasive device 132 will track as it is advanced. This graphical representation may be indicated by discrete lines and/or dots, or areas of shading or color representing the predicted confidence of the invasive device 132 location.

The screen graphics calculator 142 converts the 3D orientation and image plane intersection information into parameters which may be displayed on a Cartesian coordinate system. Scan area and screen formatting changes are communicated to the screen graphics calculator 142 via the system controller 122. This permits the needle guidance image data to be integrated with the ultrasound image data from the scan converter for display on the 2D output device, such as the display monitor 118.

The graphics drawing tool 140 applies graphical attributes to the two dimensional coordinates of the invasive device(s) 132 and imaging plane intersection(s) in order to differentiate multiple invasive devices 132 as well as target area attributes. This provides graphical feedback on the display 118 so the clinician is informed of the position and/or orientation of the invasive device(s) 132 and their potential error. In this way, the invasive device(s) 132 may be successfully advanced to the intended target. In many cases the invasive device(s) 132 may be poorly identified by their ultrasonic echoes alone, due to a poor angle of incidence to the ultrasound beam, deflection of the invasive device 132, or the construction of the invasive device 132. The graphical display, via the graphics drawing tool 140, helps the clinician direct the invasive device(s)132 when it may not be adequately visualized. Additionally, the graphical display, using the graphics drawing too 140 also gives the clinician to ability to plan the trajectory of the invasive device(s) 132 prior to inserting it into the patient. This is because the predicted trajectory, in the form of a graphical display, is overlaid onto the ultrasound image giving the clinician the opportunity to modify the transducer 104 position and/or orientation, the invasive device 132 position orientation or both prior to subjecting the patient to the invasive device 132 and potentially causing the patient further pain and discomfort.

Figure 2A:
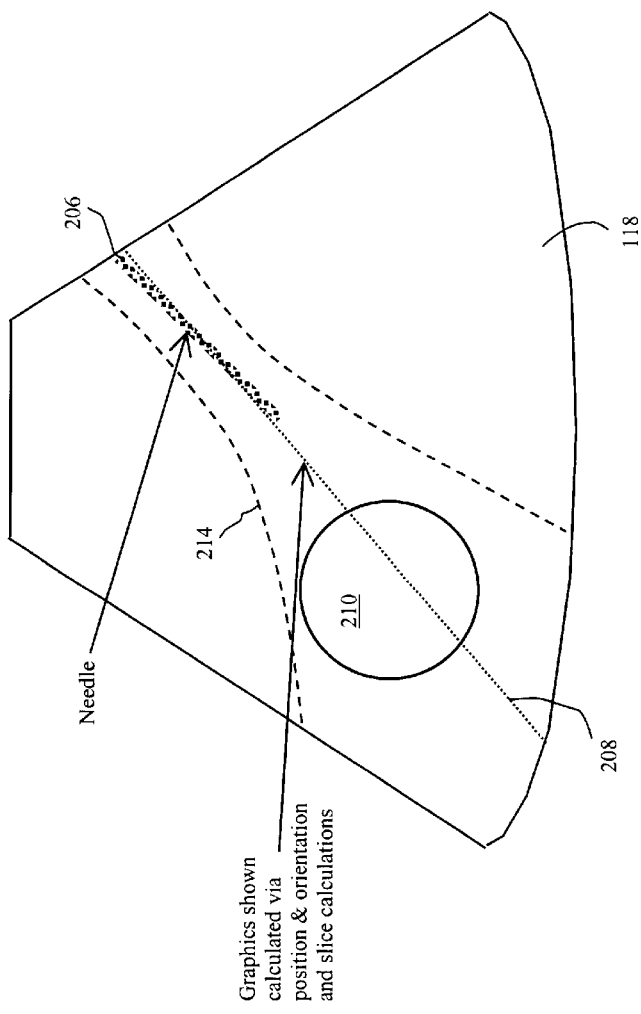
FIG. 2A depicts a representation of an invasive procedure for use with the embodiment of FIG. 1.
Figure 2B:
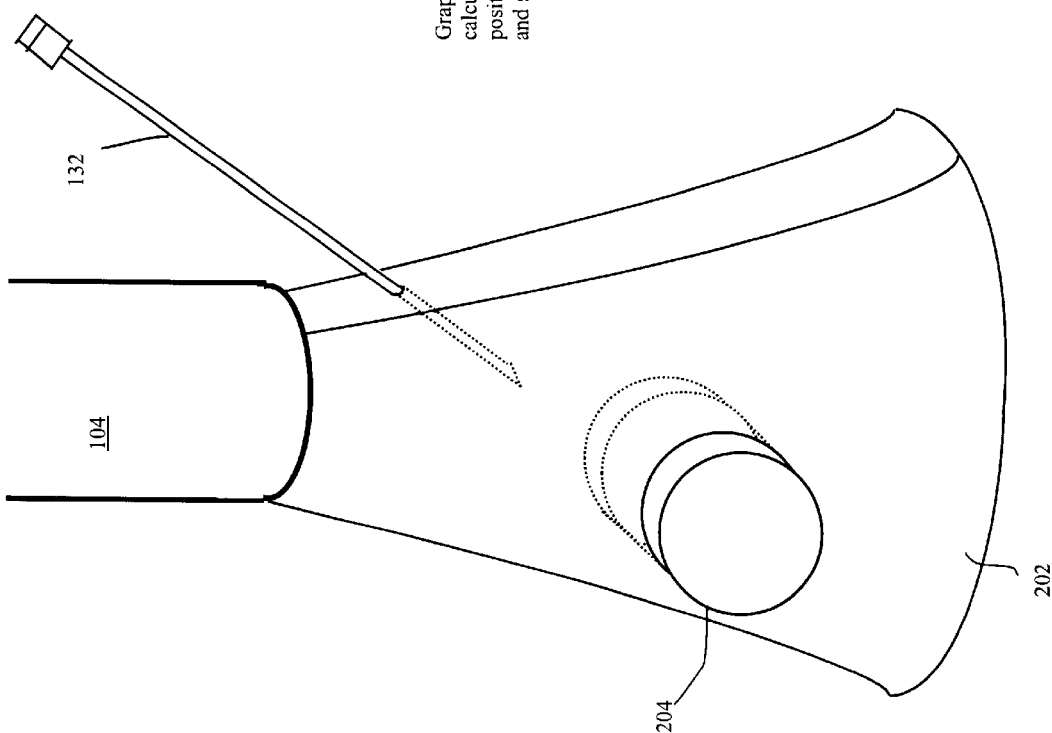
FIG. 2B depicts a representation of a diagnostic medical ultrasound display corresponding to the procedure of FIG. 2A.

Referring now to FIGS. 2A and 2B, there is shown an exemplary ultrasonic guided biopsy procedure and corresponding ultrasonic image. In this first embodiment, the position and/or orientation computation, ultrasound image beam and slice characteristics are known to the image analysis processor and display controller 116, as described above.

Consider an ultrasonic image guided biopsy of the liver. The image plane 202, also referred to herein as the scan area, scanned by the transducer 104 is oriented manually by physical movement of the transducer by the clinician (or automatically and without transducer movement as will be described below) to include the target 204 and the intended trajectory of the invasive device 132. The position and/or orientation of the invasive device 132 is indicated on the ultrasound image 118 by a graphic display 208 of the predicted pathway of the invasive device 132, accounting for the slice thickness. This prediction/display helps the clinician plan the angle and insertion location of the invasive device 132, with consideration of the slice thickness, to accurately intersect the intended target 204. It is important to consider the slice thickness in the trajectory of the invasive device 132 to the target 204 because the invasive device 132 may bend in the elevation plane similar to the way light is refracted passing between mediums of different densities, which may not be accurately represented unless accounting for the thickness of the area through which the device 132 is passing. In addition, since the ultrasound transducer 104 is usually hand held during an invasive study, the clinician may inadvertently move the ultrasound transducer solely in elevation making it possible to miss the target without any overt indication.

The disclosed system is capable of giving the clinician graphical cues which consider changes in elevation profile due to beam formation or inadvertent ultrasound transducer 104 movement. Such cues include graphical indicators, such as lines, dots, dashes, shaded and colored regions which indicate the deformation of the invasive device 132 as it passes through the ultrasound image with differing elevational thicknesses. With the disclosed embodiments, the elevation profile is known to the needle guidance system. Therefore the clinician can refer to the graphical cues generated by the guidance system to the ultrasound image 118 to modify the invasive device's 132 trajectory 208 or reposition the ultrasound probe 104. These graphical cues include indicators such as lines, dots, dashes, shaded and colored regions which indicate the predicted trajectory of the invasive device 132 and inform the clinician to the potential success of the invasive device 132 reaching the intended target. Further, the clinician is able to more clearly see the relationship between the predicted trajectory 208 as represented on the image 118 and the representation 210 of the target 204. This type of planning is not possible with externally connected needle guidance systems, therefore they fail to provide the clinician with an insight to the difficulty or ease at which they will be able to complete the procedure.

Once the planning is complete, the invasive device 132 is inserted and the actual location 206 of the leading edge of the invasive device 132 is displayed within the ultrasound image 118 along with the representation 210 of the target 204. This invasive device 132 is indicated by a graphical display 206 in the image 118. As the ultrasound transducer 104 and invasive device 132 are manipulated in space, the predicted 208 and actual trajectories 206 of the invasive device 132 are updated in real-time, at discrete intervals, or under the control of the clinician. If the ultrasound transducer 104 strays from the predicted 208 and/or actual trajectory 206 of the invasive device 132, the graphical displays 206, 208 will deform to convey the exiting of the invasive device 132 from the field of view. This includes any deformation in the elevation—or slice thickness-plane.

Figure 3:
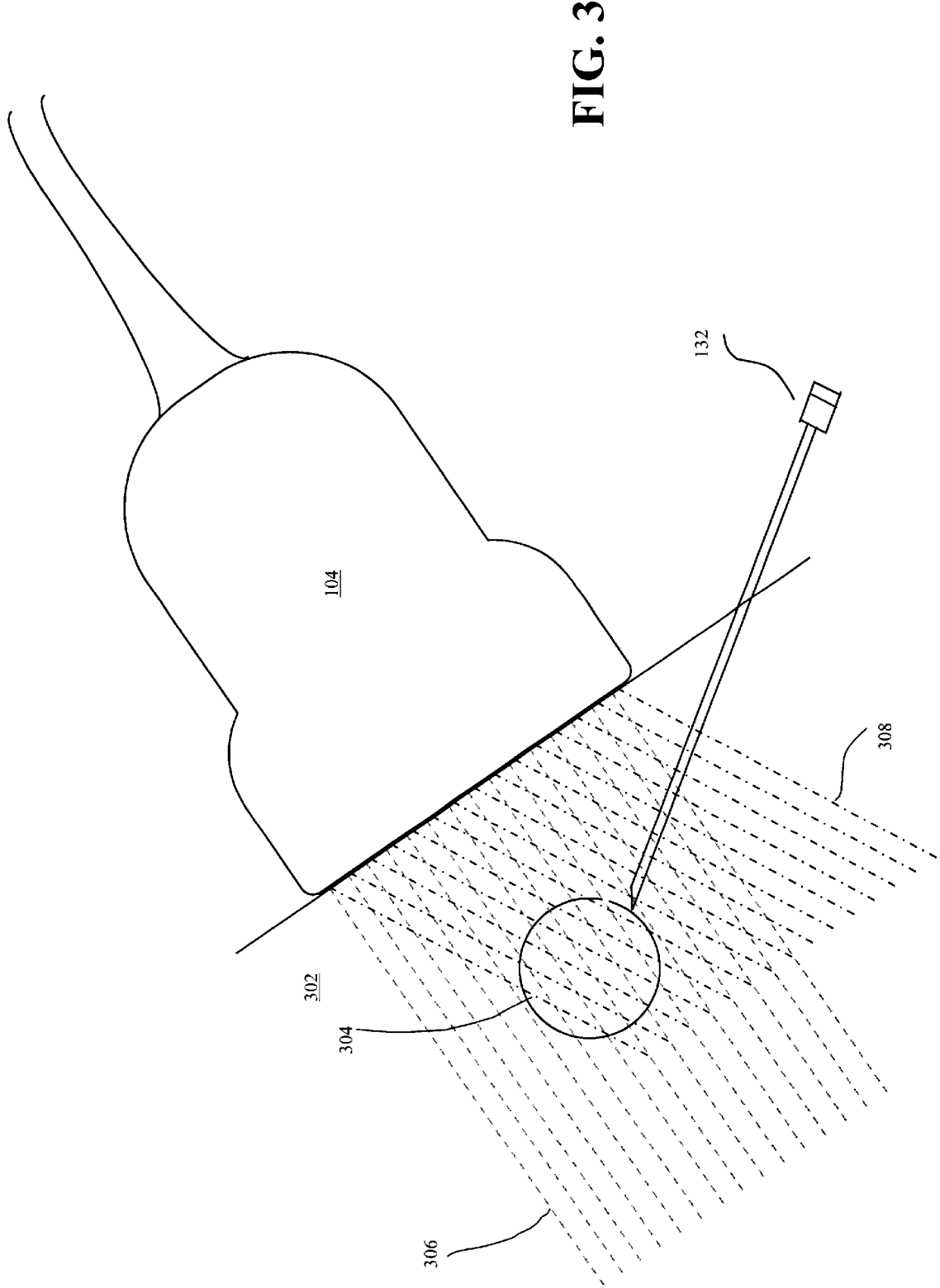
FIG. 3 depicts a representation of an invasive procedure in which the ultrasound beam is modified according to a second embodiment.
Figure 6A:
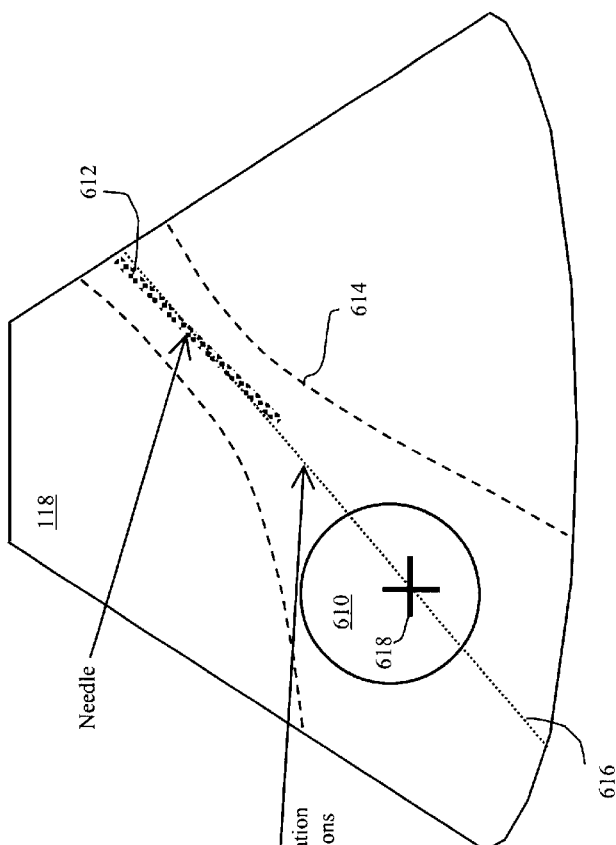
FIG. 6A depicts a representation of an invasive procedure showing the corresponding beam profile of the ultrasound device according to a fourth embodiment.
Figure 6B:
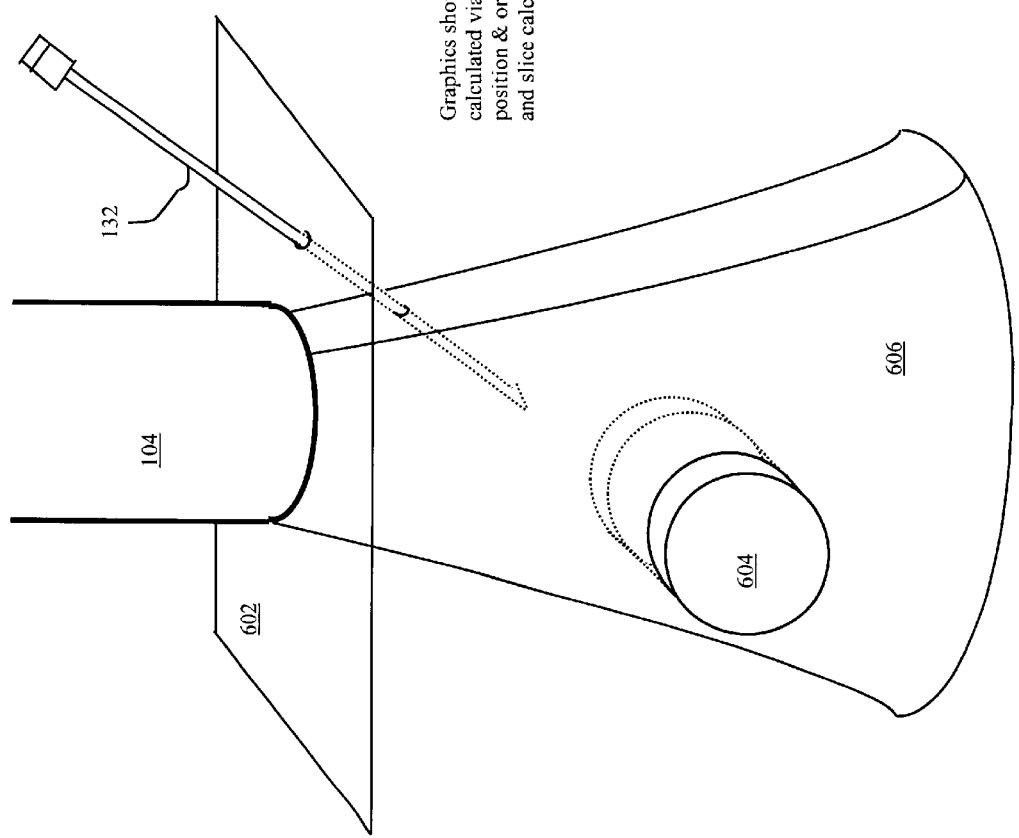
FIG. 6B depicts a graphical representation of a diagnostic medical ultrasound image corresponding to the invasive procedure of FIG. 6A according to the fourth embodiment.

Referring now to FIG. 3, there is shown an transducer probe 104 for use with a second embodiment of the system 100 which improves the imaging of the invasive device 132 by providing the capability to steer the ultrasound beam emitted by the transducer 104 without moving the transducer 104. In this second embodiment, the position and/or orientation computation, ultrasound image beam and slice characteristics are known to the image analysis processor and display controller 116 and also to the system controller 122. An ultrasound image frame can be obtained in which the ultrasound beam 306 can be aligned, i.e. steered, to be more perpendicular 308 to the angle of the invasive device's 132 trajectory. FIG. 3 demonstrates steering the ultrasonic beam within the azimuthal dimension of the imaging plane, maintaining an imaging plane perpendicular to the face of the transducer. Beam steering in the elevational dimension, wherein the imaging is non-perpendicular to the transducer face, alone or in combination with azimuthal beam steering, is also contemplated and described below. One method of controlling this beam steering or angle gives the clinician, via the user interface 120, control of the ultrasound beam 308 angle for better acoustic reflection of the invasive device 132. For example, a control knob, slider or joystick may be provided to control beam angle or the beam angle may be controlled via a displayed graphic user interface. When the ultrasound beam 306 is aligned more perpendicular 308 to the invasive device 132, the reflection from the invasive device 132 has a higher amplitude echo back to the transducer 104. This provides better visualization by the clinician of the invasive device 132 for monitoring and directing the trajectory of the invasive device 132. Another method of beam alignment control utilizes known position and/or orientation information about the invasive device 132. The position and/or orientation information is communicated to the system controller 122 to automatically revise the beam angle 308 by directing the transmit beamformer 102, receive beamformer 106, filter block 108, and signal processor 110, to modify the ultrasound beam 308 more perpendicularly to invasive device 132. Since the angle of the invasive device 132 can vary and it's position and/or orientation is known, the beam angle of the ultrasound image can be updated accordingly in real time, at discrete intervals or under the control of the clinician, as the invasive device 132 changes position and/or orientation. The optimal invasive device 132 visualization beam orientation 308 may be dynamically interleaved with the conventional ultrasound beam orientation 306, optimal for visualizing the target area, for practical clinical imaging. Line, group of line, frame and group of frame interleaving may be used. This type of integrated ultrasound beam modification 308 based on the position and/or orientation of the invasive device 132 allows for optimal viewing of both the invasive medical device 132 and the imaged portion of the subject. Graphical displays (not shown) indicate the predicted and actual trajectories 208, 214, 206 of the invasive device 132, as described.

Referring now to FIGS. 4A, 4B, 5A and 5B, there is shown an invasive procedure for use with a third embodiment of the ultrasound system 100 with integrated needle guidance functionality. As referenced in the above embodiments, the position and/or orientation computation, ultrasound image beam and slice characteristics are known to the image analysis processor and display controller 116. The ultrasound system 100 further includes an ultrasound transducer 104 that is capable of elevation focusing. Elevation focusing, as described above, permits the narrowing of the image slice for the purpose of minimizing elevational ambiguity in the displayed image. The ultrasound slice profile and the position and/or orientation of the invasive device 132 is also known by the system controller 122 of the ultrasound system 100. The beam formation is controlled by the transmit and receive beamformers 102, 106, under direction of system controller 122, in order to optimize the ultrasound image slice profile 402, 406 for better visualization of the invasive device 132 while minimizing elevational ambiguity. Optimizing the image slice by reducing the elevational thickness of the image slice further reduces the inclusion of spurious echoes around the invasive device 132, therefore insuring the voxel of ultrasound data includes primarily the reflection of the invasive device 132. This improves the contrast in displayed intensity between the invasive device 132 and the surrounding tissue. As described in the previous embodiments, improved visualization of the invasive device 132 is paramount to the clinician successfully performing an invasive ultrasound image guided procedure. Non-integrated guidance systems are unable to feed back their guidance data to the ultrasound system to control elevation image content or optimize the ultrasound image slice profile 406 based on the position and/or orientation of the invasive device 132. This reduces the clinician's ability to visualize the invasive device 132, which increases the risk of missing the intended target 404, 408.

FIG. 4A shows the normal image slice profile 402. FIG. 4B shows the optimized, narrower image slice profile 406. FIG. 5A shows the normal 502 and optimized 504 slice profiles interleaved to provide optimized visualization of the invasive device 132 and the target 506. Referring to FIG. 5B, the graphical image display 118 indicates the predicted 514 and actual trajectories 510 of the invasive device 132 as well as the target image 512. To further improve a clinician's ability to visualize the invasive device, the beam steering capability described above and shown in FIG. 3 may be combined with the embodiments in FIGS. 4A, 4B, 5A and 5B. The ability to align the ultrasound image 306 more perpendicularly 308, while narrowing the beam profile 406 by using the known position and/or orientation of the invasive device 132 further augments visualization of the invasive device 132 as described.

Referring now to FIGS. 6A, 6B, 7A and 7B, there is shown a fourth embodiment utilizing a two dimensional ("2D") transducer array 104. The 2D ultrasound transducer array 104 is under system control and is capable of re-orienting the image plane 606 and beam angle created by the transducer 104. 2D Arrays are typically used to acquire 3D images. 2D arrays can also be used to acquire 2D images. In the case of acquiring 2D images with a 2D array, there are a number of advantages:

- the frame rate can be very high because only 2D images are acquired;
- the elevation slice thickness can be controlled tightly at all depths such that more uniform elevation resolution can be achieved as compared to a conventional 2D image acquired using a one dimensional (1D) array; and
- the image plane 606 can be arbitrarily oriented.

Figure 7B:
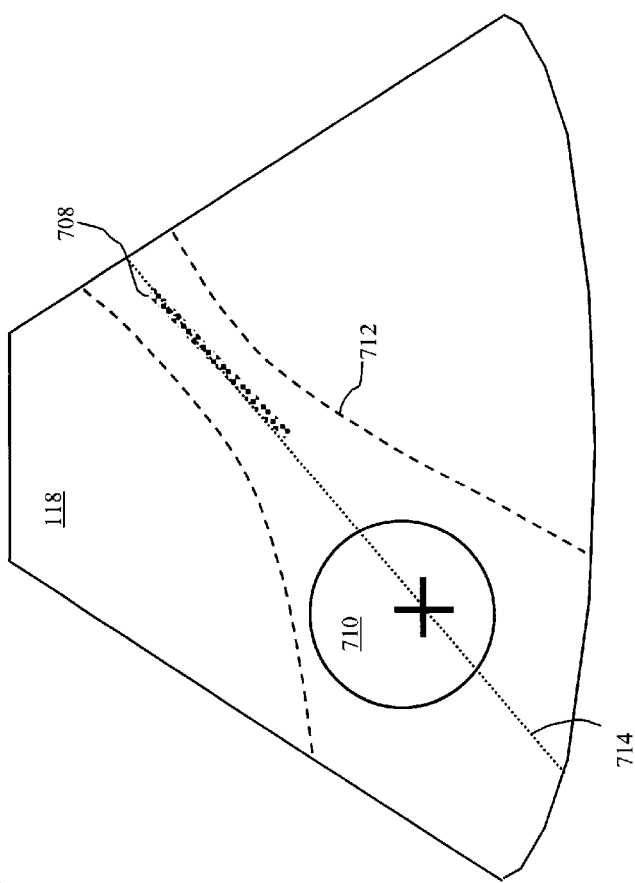
FIG. 7B depicts a graphical representation of a diagnostic medical ultrasound image corresponding to the procedure of FIG. 7A according to the fourth embodiment.
Figure 7A:
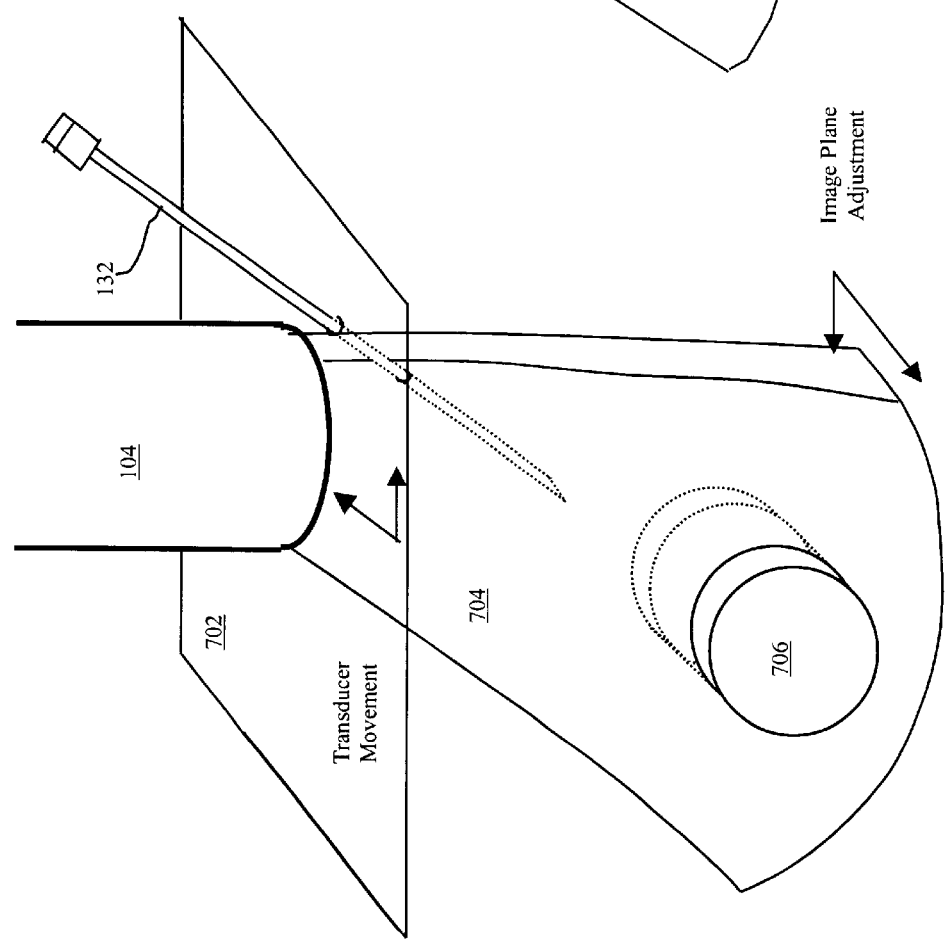
FIG. 7A depicts a representation of an invasive procedure using an ultrasound device capable of modifying the ultrasonic beam profile according to the fourth embodiment.
Figure 8A:
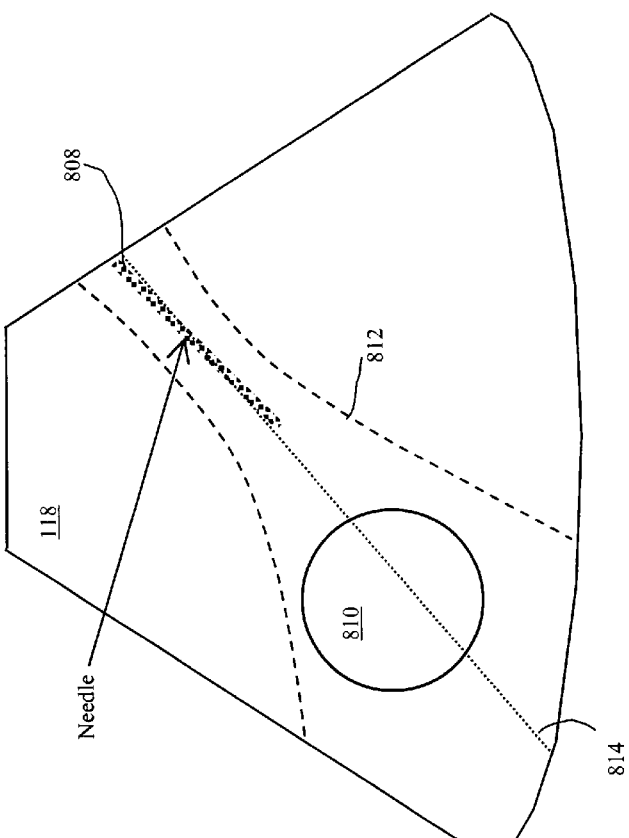
FIG. 8A depicts a representation of an invasive procedure according to a fifth embodiment showing the ultrasonic beam profile in a first orientation.
Figure 8B:
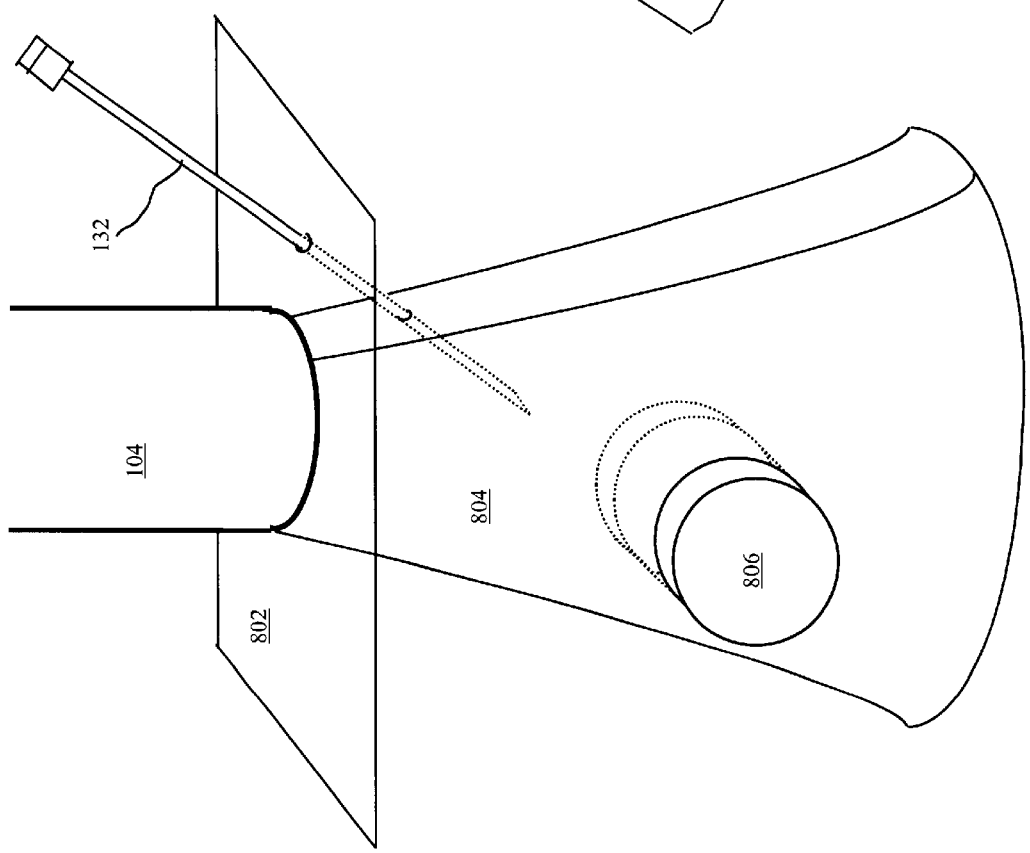
FIG. 8B depicts a graphical representation of a diagnostic medical ultrasound image corresponding to the beam profile shown in FIG. 8A according to the fifth embodiment.

The fact that imaging plane 606 can be arbitrarily oriented has, itself, a number of advantages. In the aforementioned biopsy, as the clinician advances the invasive device 132, the position and/or orientation of the ultrasound transducer 104, invasive device 132, image plane 606 as well as the beam orientation is determined and provided to the system controller 122. The clinician can mark the target 610 in the ultrasound image 118 with a graphical reference indicator 618 for which the position and/or orientation is now known by the system 100 to fix the target location. As the clinician advances the invasive device 132, the ultrasound image plane 606, beam orientation, predicted 616 and actual 612 trajectory are modified in real-time, at discrete intervals or under the control of he clinician, for accurate tracking. The ultrasound image 118 is fixed relative to the marked target 610, 618 and invasive device 132 even as the ultrasound transducer 104 is moved during the natural course of an invasive ultrasound image guided study. Referring to FIG. 7A, this is achieved by the ultrasound system 100 either automatically or under the control of the clinician via the user interface 120. The ultrasound system 100 aligns the image plane 704 to a plane which includes the predicted 714 and actual 708 trajectory of the invasive device 132 and the indicated target 716. This alignment of the imaging plane 704 may be achieved through beam steering in the azimuthal and/or elevational dimensions as has been described. Graphically, this is shown in FIG. 7B showing that the image of the invasive device 132 and target 710 is maintained similarly as that of FIG. 6B despite movement of the transducer 104. In this way, the clinician maintains consistent real-time monitoring of the invasive device 132 and confirmation of accurate placement. As indicated previously, prior art embodiments do not access ultrasound system 100 beam formation and processing information, so cannot improve the success of an ultrasound image guided biopsy by the means described.

Referring now to FIGS. 8A, 8B, 9A and 9B, there is shown a fifth embodiment, using an aforementioned 2D or rotational array 104 (such as is used in a transesophageal transducer) where the position and/or orientation of the transducer 104, image plane 804, beam orientation, and invasive device 132 is known. As the clinician advances the biopsy device 132 the display 118 indicates the predicted 814 and actual 808 trajectory overlaid over the ultrasound image 118 via graphical means, as described. When using this embodiment, the position and/or orientation of the ultrasound beam and invasive device 132 is known. The clinician can indicate via user interface control whether or not to image the needle 132 in it's longitudinal axis or to rotate the plane 904 of the image, as shown in FIGS. 9A and 9B, to the short axis for visualization of the needle 132 tip 910. This allows the clinician the full confidence and opportunity to visualize the progress of the invasive device 132 in two planes 804, 904 under ultrasound image guidance which is not possible with prior art embodiments. In one embodiment, the imaging planes are maintained perpendicular to the transducer 104 face. In an alternate embodiment, one or both imaging planes are also steered in the azimuthal and/or elevational dimensions for further optimized viewing and/or tracking of the device 132 tip 910.

Figure 10:
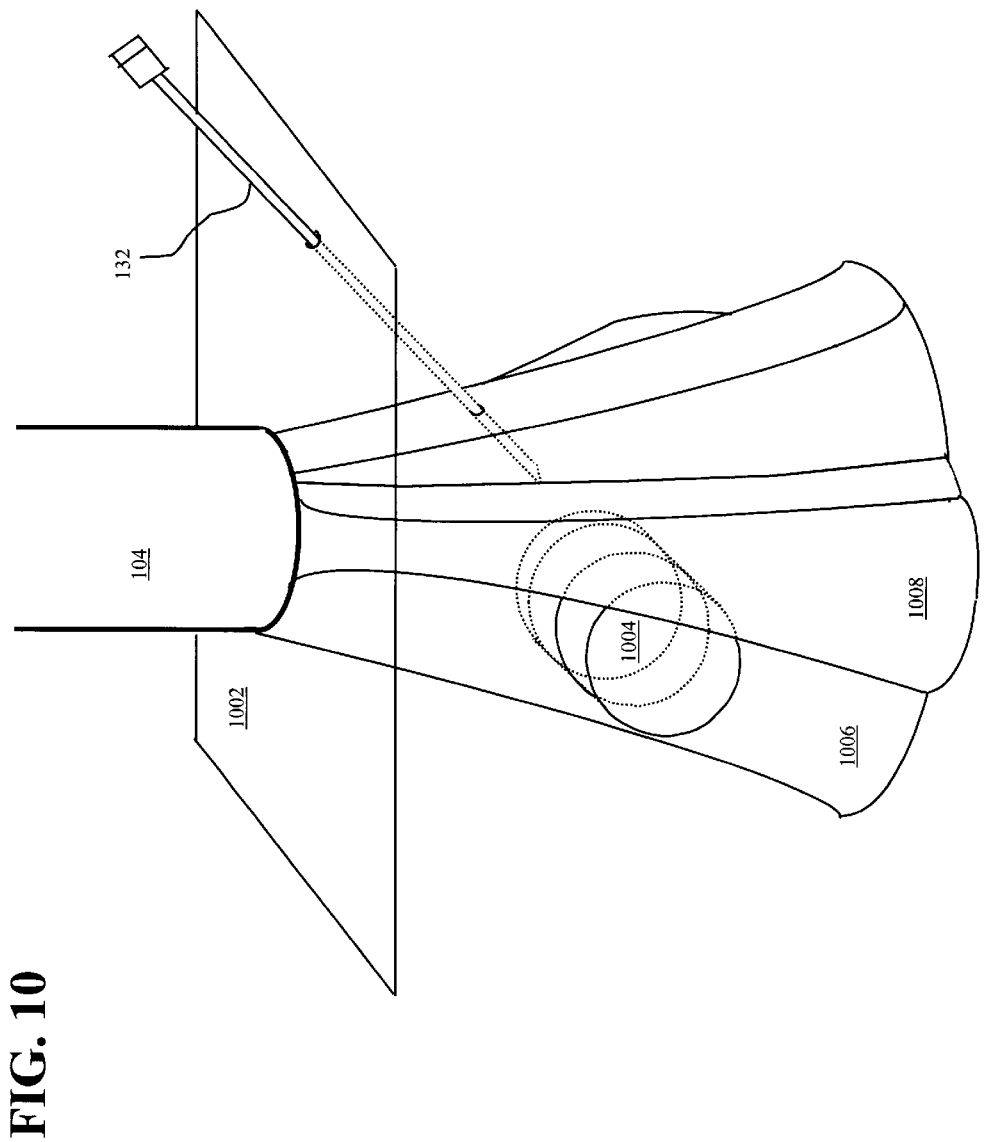
FIG. 10 depicts a representation of an invasive procedure using an ultrasound device with interleaved beam profiles orthogonal in orientation, according to a sixth embodiment.
Figure 11B:
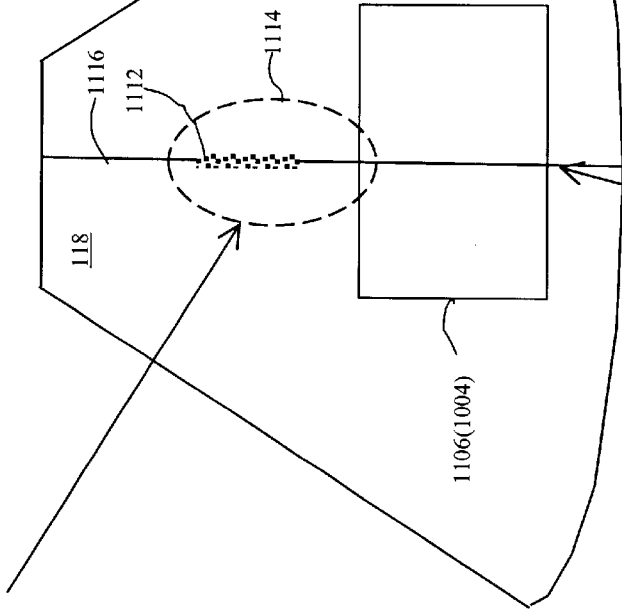
FIGS. 11A and 11B depict a graphical representation of a side by side diagnostic medical ultrasound images corresponding to the procedure of FIG. 10 produced by the beam profiles depicted in FIG. 10, according to the sixth embodiment.
Figure 11A:
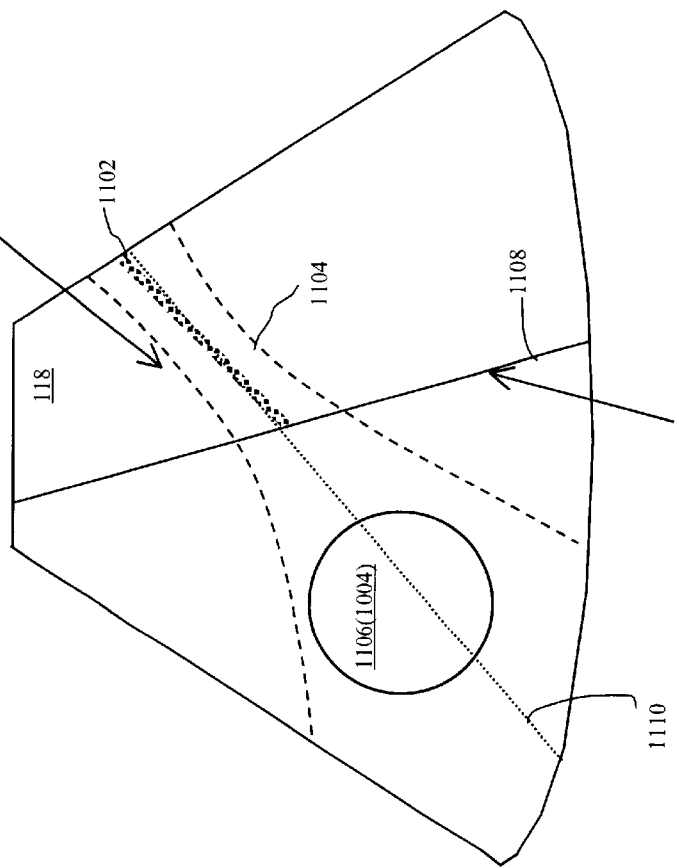

Referring now to FIGS. 10, 11A and 11B, there is shown a sixth embodiment, using the aforementioned rotational 2D array where the position and/or orientation of the ultrasound transducer 104, image plane 1006, 1008, beam orientation, and invasive device 132 is known. The clinician can mark the position and/or orientation of the target 1004 with a graphical indicator in which the position and/or orientation is marked for reference in the ultrasound image. See FIGS. 11A and 11B. As the clinician advances the invasive device 132, two imaging planes 1006, 1008 are formed to image 1) the plane of the needle 132 path to the target 1004, and 2) a plane that tracks the needle 132 tip in cross-section. The needle 132 insertion to target plane 1006 is fixed to include the marked target 1106 and the invasive device 132. This plane remains 1006 intact even though the ultrasound transducer 104 is moved during the course of the biopsy. The second plane 1008 is formed at an angle to the first plane's 1006 azimuth dimension. This angle is preferably perpendicular in azimuth to the first image plane 1006. As the biopsy device 132 is advanced towards the target 1004, the second plane 1008 sweeps through the body, always located at the predicted 1110, 1116 and actual 1102, 1112 trajectory of the invasive device 132 tip yet maintaining perpendicular placement to the first plane 1006. The first 1006 and/or second 1008 planes may also be steered in the azimuthal and/or elevational dimensions for further optimal viewing and/or tracking. It is important to the clinician to identify the invasive device 132 tip, as this is the leading edge of the invasive device 132 and determines accurate placement towards the intended target 1004, 1106. These two frames would be displayed as separate images 118 on one display on the ultrasound system 100. As in aforementioned embodiments, the predicted and actual trajectories 1102, 1112, 1104, 1110, 1114, are indicated graphically in each ultrasound image 118 in FIGS. 11A and 11B. An additional display element is provided which is a graphical identification of the first plane 1006 and second planes 1008 as planer orientation markers 1116, 1108 respectively. This provides the clinician with a reference of where the first plane 1006 is located in reference to the second plane 1008 and the second plane location in reference to the first plane 1006. Plane references are important to the clinician when multiple ultrasound image planes are presented on one display 118. This allows one to quickly interpret two distinctly different views of objects within the ultrasound image 118 giving confidence of position and/or orientation during an ultrasound guided invasive procedure.

Figure 12:
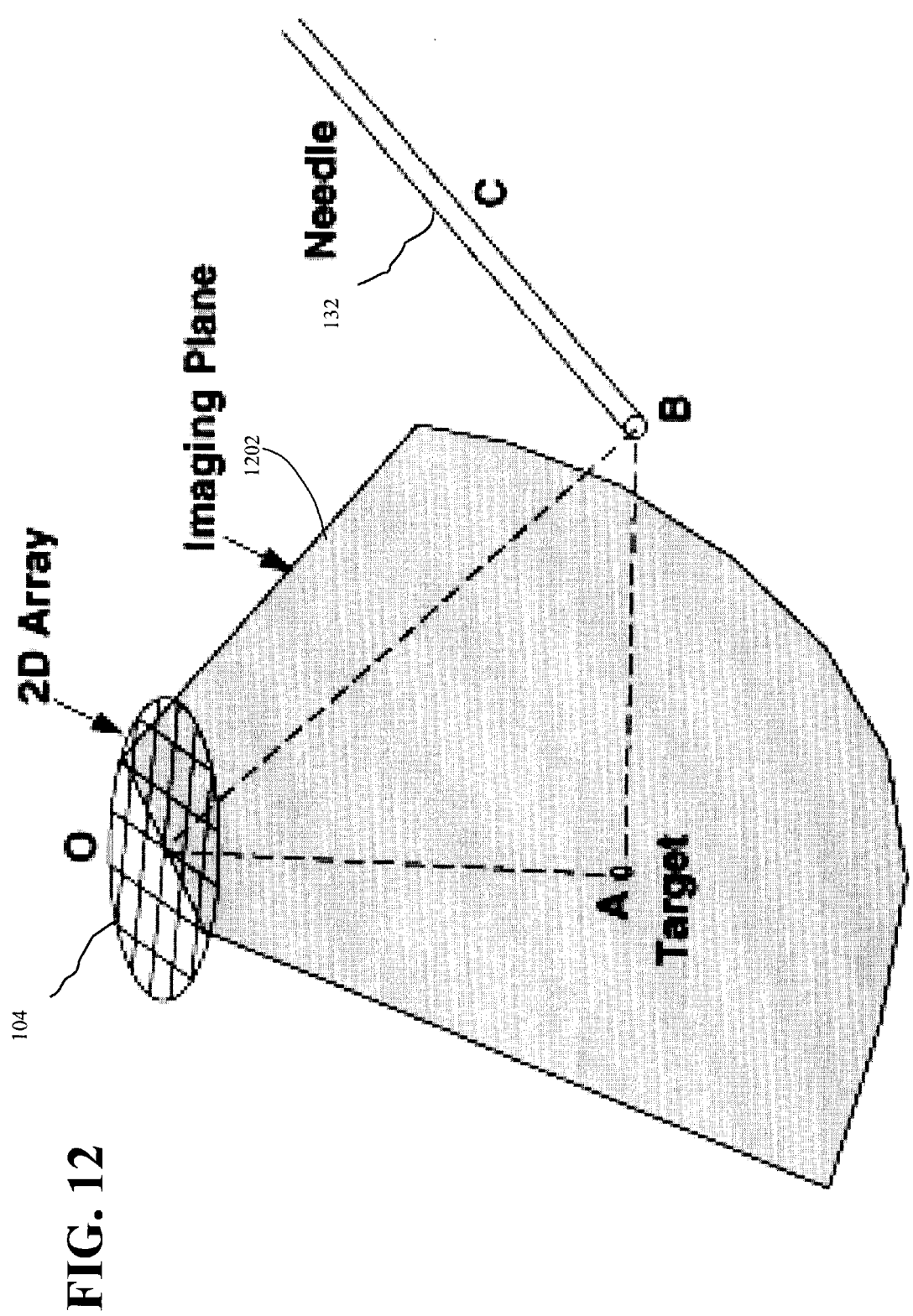
FIG. 12 depicts a graphical representation of an invasive procedure using a 2D array ultrasound device with a corresponding imaging plane, according to a seventh embodiment.

Referring now to FIGS. 12–14 and 15A, 15B and 15C, there is shown a seventh embodiment allowing the clinician to optimally view the target and invasive medical device, as well as the projected and actual trajectories of the invasive medical device, relative to a common reference, such as the tip, or other portion, of the invasive medical device. Consider the application of a breast biopsy using a needle 132. Referring to FIG. 12, there is shown a 2D transducer array 104 acquiring a 2D image 1202 containing a target, labeled "A". A biopsy needle 132, labeled "BC", needs to be inserted so that the tip, labeled "B" is eventually at the target, A. Let the center of the 2D array 104 be "O". The plane OAB is not the same as the imaging plane 1202. The system 100 can automatically detect the location of point A by analyzing the imaging plane 1202. An exemplary method of accomplishing this detection may include the following:

1. The user views the 2D image plane 1202 on the screen and selects point A using a cursor, caliper or other indicator via the user interface 120 to designate the target location in space. The output of this action is the coordinates of the point A in the image plane 1202.
2. The system 100 knows the location and orientation of the image plane 1202 in the 3D space because it fired ultrasonic lines on the image plane 1202.
3. Using the location and orientation of the image plane 1202 in the 3D space and the 2D coordinates of the point A, the system 100 computes the location of the point A in the 3D space.

An active or passive position or orientation sensor can also tell the system the location of the tip B. The system can then steer the imaging plane 1202 such that the imaging plane 1202 is identical to the plane OAB.

Figure 13:
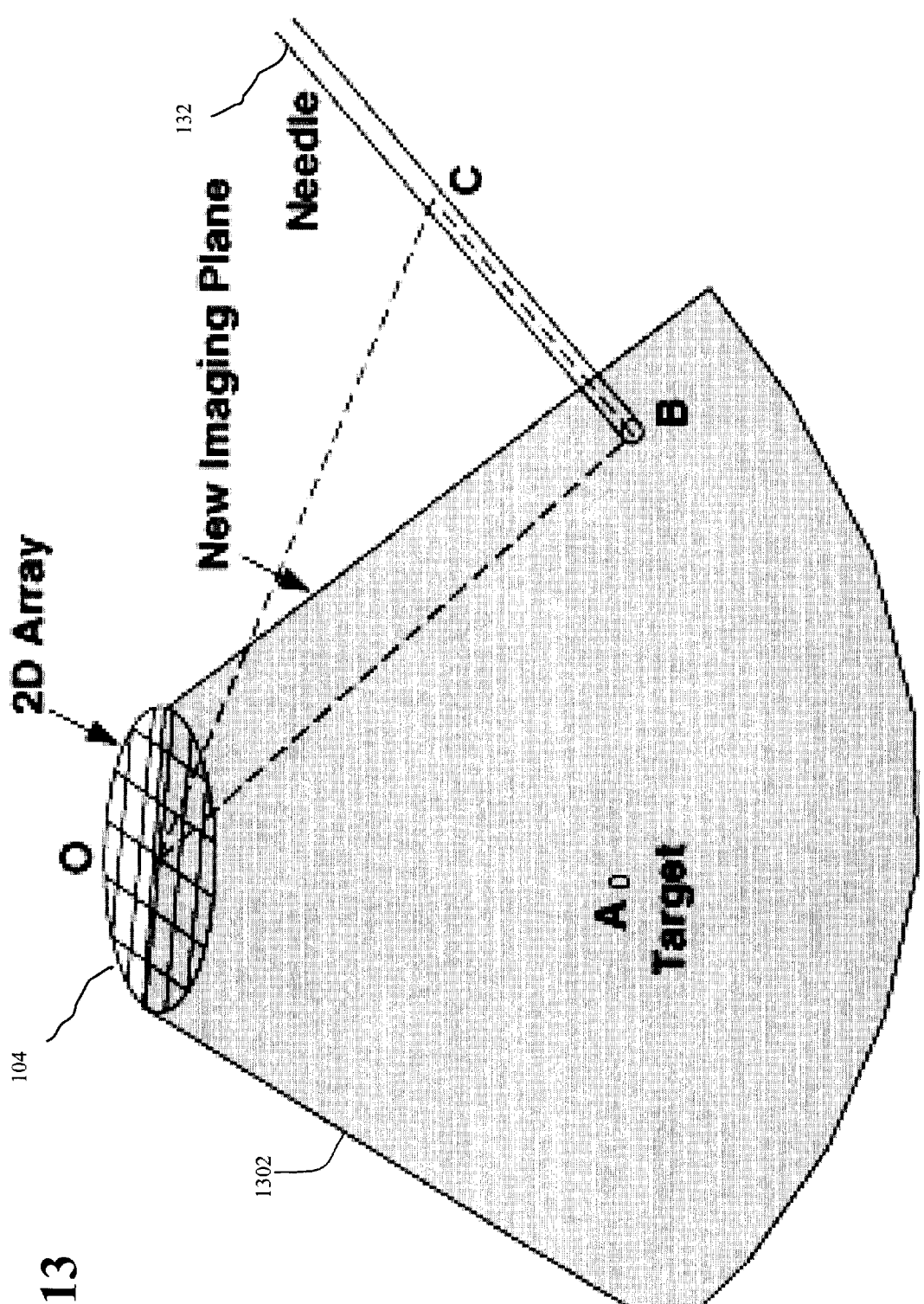
FIG. 13 depicts a graphical representation of the invasive procedure of FIG. 12 using a 2D array diagnostic ultrasound device depicting the calculated position and orientation of a new imaging plane according to the seventh embodiment.

This adjusted imaging plane 1302 is shown in FIG. 13. The user can now visualize the target A and the tip of the needle 132, B at the same time automatically wherever the tip and the target are in the physical space. However, the axis of the needle 132, BC, is still not visible in the image since plane OBC is not the same as the imaging plane 1302, OAB. Knowing the location of point C (any point on the needle 132 other than the tip) using an active or passive position or orientation sensing method, the system 100 can also steer the imaging plane 1302 to the plane OBC.

Figure 14:
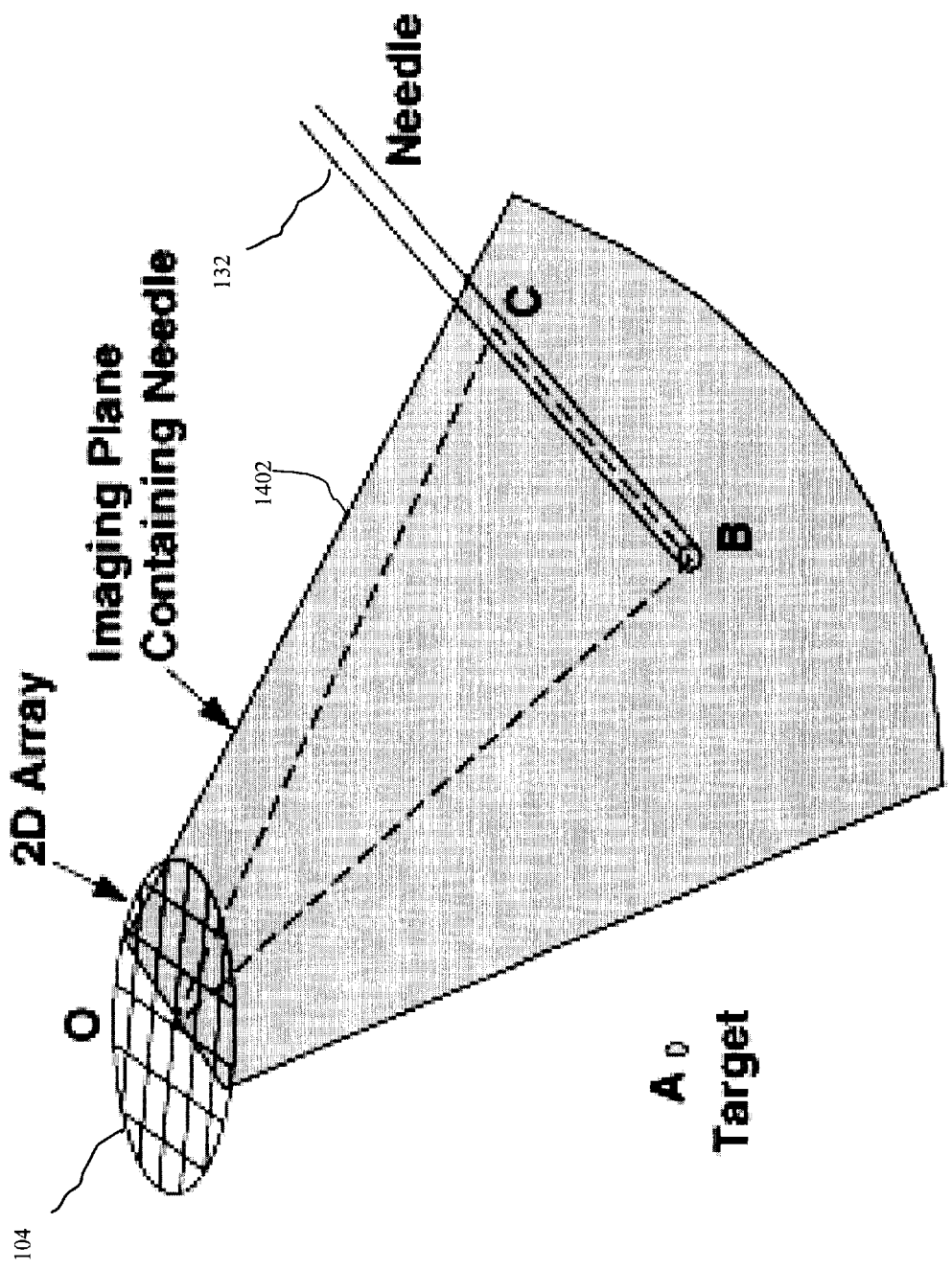
FIG. 14 depicts a graphical representation of the invasive procedure of FIG. 12 using a 2D array diagnostic ultrasound device, depicting the modified position and orientation of the imaging plane according to the seventh embodiment.

This is shown in FIG. 14 as imaging plane 1402. The user can now visualize the needle 132, BC automatically, wherever the needle 132 is in the physical space. Note that plane OAB and OBC are not the same plane. Therefore, in order to visualize the target A, the needle 132 tip B and the needle 132 axis BC, the system 100 acquires planes OAB and OBC in an interleaved fashion. In this way, imaging is optimized relative to the common reference between the planes, i.e., the tip B.

FIGS. 15A–C show one possible display of these interleaved imaging planes on the screen. FIG, 15A shows plane OAB while FIG. 15B shows plane OBC. Note that line OB is common to both planes. FIG. 1 SC shows a way to present the spatial relationships of the target A, the tip B and the needle 132, BC to the user. When the user reaches the target, A=B, i.e., as the tip of the invasive device 132 comes closer to the target, the two separate planes will converge into one plane when the tip (A) meets the target (B) in the same position and/or orientation.

In addition, invasive medical implements of the type described herein are typically somewhat flexible in their structure. As they are inserted into the subject, they tend to bend or deflect. This deflection will cause divergence in the projected trajectory of the implement from the actual trajectory. The projected trajectory is computed under the assumption that the invasive implement, i.e. its orientation, will remain straight and not bend as it is inserted into the body. The disclosed embodiments compensate for deviations in the actual trajectory of the invasive device to properly compute the projected trajectory. The amount of deflection is dependent upon the hardness of the medium, the homogeneity of the medium, and the characteristics of the invasive device such as its thickness or gauge, the material it is fabricated from and its structure. Further, the degree of deflection is also dependent upon the clinician's insertion technique and the amount of manipulation imparted on the device during insertion. The disclosed embodiments can utilize invasive devices which are bendable or deformable or rigid. Further the invasive device may have a straight, curved or other profile.

In addition, while the ultrasound slice is not altered by the invasive device as it enters the subject (i.e., the same portion is imaged by the transducer whether the invasive device is present or not providing the transducer is not moved and other settings do not change), the portion of the subject being imaged may deform as the invasive device encounters and/or passes through. In this case, the target location will be deformed due to the Z-axis component of the slice. In one alternate embodiment, this deformation is represented on the display as a non-symmetrical trajectory line to accurately depict the slice non-uniformity.

In still other alternative embodiments, multiple invasive devices are used substantially simultaneously, such as in laproscopic procedures. In such embodiments, the position and/or orientation of each device is discretely displayed relative to and within the imaged subject. Further, the scan area/imaging plane and/or beam characteristics, such as beam angle, may be altered in real time and interleaved so as to optimally view the target as well as all or a sub-set of the invasive medical devices in use. In still other alternative embodiments multiple imaging transducers may be utilized simultaneously, such as in intraoperative, or endocavity ultrasound imaging methodologies. In such embodiments the position and/or orientation of each transducer is identified and displayed relative to and within the imaged subject.

It is therefore intended that the foregoing detailed description be regarded as illustrative rather than limiting, and that it be understood that it is the following claims, including all equivalents, that are intended to define the spirit and scope of this invention.

We claim:

1. In a diagnostic medical ultrasound system, a method of displaying a trajectory of an invasive medical device relative to and within a portion of a subject, said method comprising:
    (a) generating an image of said portion utilizing an ultrasound transducers said transducer having at least one operational characteristic;
    (b) obtaining location information about said ultrasound transducer and said invasive medical device;
    (c) obtaining, automatically, said at least one operational characteristic of said ultrasound transducer;
    (d) computing a first trajectory of said invasive medical device relative to said portion utilizing said location information and said at least one operational characteristic; and
    (e) computing a second trajectory of said invasive medical device within said portion utilizing said location information and said at least one operational characteristic.

2. The method of claim 1, further comprising:
    (f) displaying said image of said portion on a display, said image further comprising representations of said first and second trajectories.

3. The method of claim 2, wherein said portion is characterized by having three-dimensions and said output device is characterized by having two-dimensions and further wherein (f) further comprises compensating said representations in said image for said displaying of said three-dimensional portion on said two-dimensional output device utilizing said location information and said at least one operational characteristic.

4. The method of claim 1, wherein said portion is characterized by a slice geometry and further wherein (d) and (e) further comprise obtaining data representing said slice geometry and compensating for said slice geometry based on said data.

5. The method of claim 4, wherein said compensating further comprises controlling said diagnostic medical ultrasound system to automatically adjust said slice geometry for optimal representation of said first and second trajectories.

6. The method of claim 4, further comprising:
    (f) displaying an image of said portion on a display, said image further comprising representations of said first and second trajectories; and
    wherein said compensating further comprises adjusting said representations based on said data.

7. The method of claim 4, wherein said compensating further comprises controlling said diagnostic medical ultrasound system to automatically adjust an ultrasonic beam emitted by said ultrasound transducer.

8. The method of claim 1, wherein said invasive medical device is characterized by deformability and further wherein (b) further comprises obtaining deformation information of said invasive medical device and (d) and (e) further comprise compensating for said deformation.

9. The method of claim 1, wherein said portion further comprises a target and further wherein (d) and (e) further comprise computing guidance information to guide said invasive medical device to said target.

10. The method of claim 1, wherein said image lies in an imaging plane of said ultrasound transducer, said method further comprising:
    (f) controlling said diagnostic medical ultrasound system to automatically align said imaging plane to optimize imaging of said invasive medical device based on said computed first and second trajectories.

11. The method of claim 10, wherein (f) further comprises aligning said imaging plane to be substantially at least one of parallel and perpendicular to at least one of said first and second trajectories.

12. The method of claim 10, further comprising:
(g) interleaving said imaging plane optimized for imaging said invasive medical device with an imaging plane optimized for imaging said portion.

13. The method of claim 10, wherein (f) further comprises aligning said imaging plane to a common reference between a first plane including at least one of said first and second trajectories and a second plane including said portion.

14. The method of claim 10, wherein (f) further comprises aligning said imaging plane in elevation non-perpendicular to a face of said ultrasound transducer.

15. The method of claim 10, wherein (f) further comprises rotating said imaging plane about an axis perpendicular to a face of said ultrasound transducer.

16. The method of claim 1, further comprising:
(f) controlling said diagnostic medical ultrasound system to automatically adjust an ultrasonic beam emitted from said ultrasound transducer to achieve a more perpendicular incident angle of said ultrasonic beam with said portion to said first trajectory based on said computed first and second trajectories.

17. In a diagnostic medical ultrasound system, a method of displaying a trajectory of an invasive medical device relative to and within a portion of a subject, said portion including a target portion of said invasive medical device, said method comprising:
(a) generating a first image of said portion utilizing an ultrasound transducer, said image including said target portion, said ultrasound transducer emitting ultrasonic energy according to a first beam parameter, said first beam parameter optimized to image said target portion;
(b) obtaining location information about said ultrasound transducer and said invasive medical device;
(c) computing a trajectory of said invasive medical device relative to said portion utilizing said location information;
(d) computing a second beam parameter based on said location information and said trajectory, said second beam parameter being optimized to image said invasive device;
(e) causing, automatically, said ultrasound transducer to emit ultrasonic energy according to said second beam parameter; and
(f) generating a second image of said portion utilizing said ultrasound transducer, said image including a representation of said invasive device.

18. The method of claim 17 further comprising:
(g) controlling, automatically, said diagnostic ultrasound system to optimize said first and second beam parameters to optimally view both said target portion and said invasive medical device.

19. The method of claim 17 further comprising:
(g) interleaving said first and second images on said display.

20. The method of claim 17 further comprising:
(g) alternating between said first and second images on said display.

21. The method of claim 17, wherein said computing of said second beam parameter further comprises computing a beam angle.

22. The method of claim 21, wherein said computing of said beam angle further comprises computing said beam angle to be substantially at least one of perpendicular and parallel to said invasive medical device.

23. The method of claim 17, wherein said computing of said second beam parameter further comprises computing an elevation focus.

24. The method of claim 23, wherein said computing of said elevation focus further comprises narrowing said elevation focus.

25. The method of claim 17, wherein said computing of said second beam parameter further comprises computing an image plane orientation.

26. The method of claim 25, wherein said computing of said image plane orientation further comprises orientating said image plane to be in a plane of said invasive medical device.

27. The method of claim 26, wherein said computing of said image plane orientation further comprises orientating said image plane to be in a plane of said invasive medical device and said target portion.

* * * * *